US009962465B2

(12) United States Patent
Moradian-Oldak et al.

(10) Patent No.: US 9,962,465 B2
(45) Date of Patent: May 8, 2018

(54) AMELOGENIN-CHITOSAN HYDROGEL FOR DENTIN HYPERSENSITIVITY

(71) Applicant: UNIVERSITY OF SOUTHERN CALIFORNIA, Los Angeles, CA (US)

(72) Inventors: Janet Moradian-Oldak, Los Angeles, CA (US); Qichao Ruan, Alhambra, CA (US); Kaushik Mukherjee, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days. days.

(21) Appl. No.: 15/202,882

(22) Filed: Jul. 6, 2016

(65) Prior Publication Data

US 2017/0007737 A1 Jan. 12, 2017

Related U.S. Application Data

(60) Provisional application No. 62/189,356, filed on Jul. 7, 2015.

(51) Int. Cl.

| | |
|---|---|
| ***C07K 14/47*** | (2006.01) |
| ***A61L 27/22*** | (2006.01) |
| ***A61L 27/44*** | (2006.01) |
| ***A61L 27/46*** | (2006.01) |
| ***A61L 27/52*** | (2006.01) |

(52) U.S. Cl.

CPC ........... *A61L 27/227* (2013.01); *A61L 27/446* (2013.01); *A61L 27/46* (2013.01); *A61L 27/52* (2013.01); *C07K 14/47* (2013.01); *A61L 2430/12* (2013.01)

(58) Field of Classification Search

None

See application file for complete search history.

(56) References Cited

U.S. PATENT DOCUMENTS

| | | | |
|---|---|---|---|
| 7,294,352 B2 | 11/2007 | Gestrelius et al. | |
| 2003/0104020 A1 | 6/2003 | Davison et al. | |
| 2014/0186273 A1 | 7/2014 | Moradian-Oldak et al. | |
| 2015/0065435 A1* | 3/2015 | Sarikaya ................ | C07K 14/78 514/21.4 |

FOREIGN PATENT DOCUMENTS

| | | |
|---|---|---|
| JP | 2012-167040 A | 9/2012 |

OTHER PUBLICATIONS

Mukherjee, K. et al., "Repairing human tooth enamel with leucine-rich amelogenin peptide-chitosan hydrogel," J. Mater. Res., v. 31, n. 5, Mar. 14, 2016, pp. 556-563.

* cited by examiner

*Primary Examiner* — Kartheinz R. Skowronek
*Assistant Examiner* — Ronald T Niebauer
(74) *Attorney, Agent, or Firm* — Brooks Kushman P.C.

(57) ABSTRACT

A method to regrow a protective layer over exposed/demineralized dentin that includes a step of identifying a subject having exposed/demineralized dentin. The demineralized dentin is contacted with a remineralization composition that includes an amelogenin and derived peptides, a chitosan, water, and a sufficient amount of a pH adjusting component such that the composition has a pH greater than about 6.0 such that dentinal tubules are occluded with apatite crystals and enamel is regrown on the dentinal tubules.

11 Claims, 20 Drawing Sheets

SEQUENCE LISTING

<160> NUMBER OF SEQ ID NOS: 11

<210> SEQ ID NO 1
<211> LENGTH: 189
<212> TYPE: PRT
<213> ORGANISM: Sus scrofa

<400> SEQUENCE: 1

Met Gly Thr Trp Ile Leu Phe Ala Cys Leu Leu Gly Ala Ala Phe Ser
1               5                   10                  15

Met Pro Leu Pro Pro His Pro Gly His Pro Gly Tyr Ile Asn Phe Ser
            20                  25                  30

Tyr Glu Val Leu Thr Pro Leu Lys Trp Tyr Gln Asn Met Ile Arg His
        35                  40                  45

Pro Tyr Thr Ser Tyr Gly Tyr Glu Pro Met Gly Gly Trp Leu His His
    50                  55                  60

Gln Ile Ile Pro Val Val Ser Gln Gln Thr Pro Gln Ser His Ala Leu
65                  70                  75                  80

Gln Pro His His His Ile Pro Met Val Pro Ala Gln Gln Pro Gly Ile
                85                  90                  95

Pro Gln Gln Pro Met Met Pro Leu Pro Gly Gln His Ser Met Thr Pro
            100                 105                 110

Thr Gln His His Gln Pro Asn Leu Pro Leu Pro Ala Gln Gln Pro Phe
        115                 120                 125

Gln Pro Gln Pro Val Gln Pro Gln Pro His Gln Pro Leu Gln Pro Gln
    130                 135                 140

Ser Pro Met His Pro Ile Gln Pro Leu Leu Pro Gln Pro Pro Leu Pro
145                 150                 155                 160

Pro Met Phe Ser Met Gln Ser Leu Leu Pro Asp Leu Pro Leu Glu Ala
                165                 170                 175

Trp Pro Ala Thr Asp Lys Thr Lys Arg Glu Glu Val Asp
            180                 185

<210> SEQ ID NO 2
<211> LENGTH: 184
<212> TYPE: PRT
<213> ORGANISM: Bos taurus

<400> SEQUENCE: 2

Phe Ala Cys Leu Leu Gly Ala Ala Tyr Ser Met Pro Leu Pro Pro His
1               5                   10                  15

Pro Gly His Pro Gly Tyr Ile Asn Phe Ser Tyr Glu Val Leu Thr Pro
            20                  25                  30

Leu Lys Trp Tyr Gln Asn Met Leu Arg Tyr Pro Tyr Pro Ser Tyr Gly
        35                  40                  45

Tyr Glu Pro Val Gly Gly Trp Leu His His Gln Ile Ile Pro Val Val
    50                  55                  60

Ser Gln Gln Ser Pro Gln Asn His Ala Leu Gln Pro His His His Asn
65                  70                  75                  80

Pro Met Val Pro Ala Gln Gln Pro Val Val Pro Gln Gln Pro Met Met
                85                  90                  95

Pro Val Pro Gly Gln His Ser Met Thr Pro Ile Gln His His Gln Pro
            100                 105                 110

Asn Leu Pro Leu Pro Ala Gln Gln Ser Phe Gln Pro Gln Pro Ile Gln
        115                 120                 125

Pro Gln Pro His Gln Pro Leu Gln Pro Gln Pro Pro Val His Pro Ile

```
    130                 135                 140

Gln Arg Leu Pro Pro Gln Pro Pro Leu Pro Pro Ile Phe Pro Met Gln
145                 150                 155                 160

Pro Leu Pro Pro Val Leu Pro Asp Leu Pro Leu Glu Ala Trp Pro Ala
                165                 170                 175

Thr Asp Lys Thr Lys Arg Glu Glu
            180


<210> SEQ ID NO 3
<211> LENGTH: 191
<212> TYPE: PRT
<213> ORGANISM: Homo sapiens

<400> SEQUENCE: 3

Met Gly Thr Trp Ile Leu Phe Ala Cys Leu Leu Gly Ala Ala Phe Ala
1               5                   10                  15

Met Pro Leu Pro Pro His Pro Gly His Pro Gly Tyr Ile Asn Phe Ser
            20                  25                  30

Tyr Glu Val Leu Thr Pro Leu Lys Trp Tyr Gln Ser Ile Arg Pro Pro
        35                  40                  45

Tyr Pro Ser Tyr Gly Tyr Glu Pro Met Gly Gly Trp Leu His His Gln
    50                  55                  60

Ile Ile Pro Val Leu Ser Gln Gln His Pro Pro Thr His Thr Leu Gln
65                  70                  75                  80

Pro His His His Ile Pro Val Val Pro Ala Gln Gln Pro Val Ile Pro
                85                  90                  95

Gln Gln Pro Met Met Pro Val Pro Gly Gln His Ser Met Thr Pro Ile
            100                 105                 110

Gln His His Gln Pro Asn Leu Pro Pro Pro Ala Gln Gln Pro Tyr Gln
        115                 120                 125

Pro Gln Pro Val Gln Pro Gln Pro His Gln Pro Met Gln Pro Gln Pro
    130                 135                 140

Pro Val His Pro Met Gln Pro Leu Pro Pro Gln Pro Pro Leu Pro Pro
145                 150                 155                 160

Met Phe Pro Met Gln Pro Leu Pro Pro Met Leu Pro Asp Leu Thr Leu
                165                 170                 175

Glu Ala Trp Pro Ser Thr Asp Lys Thr Lys Arg Glu Glu Val Asp
            180                 185                 190


<210> SEQ ID NO 4
<211> LENGTH: 198
<212> TYPE: PRT
<213> ORGANISM: Pongo pygmaeus

<400> SEQUENCE: 4

Ala Cys Leu Leu Gly Ala Ala Phe Ala Met Pro Leu Pro Pro His Pro
1               5                   10                  15

Gly His Pro Gly Tyr Ile Asn Phe Ser Tyr Glu Asn Ser His Ser Gln
            20                  25                  30

Ala Ile Asn Val Asp Arg Thr Ala Leu Val Leu Thr Pro Leu Lys Trp
        35                  40                  45

Tyr Gln Ser Ile Arg Pro Pro Tyr Pro Ser Tyr Gly Tyr Glu Pro Met
    50                  55                  60

Gly Gly Trp Leu His His Gln Ile Ile Pro Val Leu Ser Gln Gln His
65                  70                  75                  80

Pro Pro Thr His Thr Leu Gln Pro His His His Ile Pro Val Val Pro
```

```
                85                  90                  95

Ala Gln Gln Pro Val Ile Pro Gln Gln Pro Met Met Pro Val Pro Gly
            100                 105                 110

Gln His Ser Met Thr Pro Thr Gln His His Gln Pro Asn Leu Leu Pro
        115                 120                 125

Pro Ala Gln Gln Pro Tyr Gln Pro Gln Pro Val Gln Pro Gln Pro His
    130                 135                 140

Gln Pro Met Gln Pro Gln Pro Pro Val His Pro Met Gln Pro Leu Pro
145                 150                 155                 160

Pro Gln Pro Pro Leu Pro Pro Met Phe Pro Met Gln Pro Leu Pro Pro
                165                 170                 175

Met Leu Pro Asp Leu Thr Leu Glu Ala Trp Pro Ser Thr Asp Lys Thr
            180                 185                 190

Lys Arg Glu Glu Val Asp
        195


<210> SEQ ID NO 5
<211> LENGTH: 205
<212> TYPE: PRT
<213> ORGANISM: Pan troglodytes

<400> SEQUENCE: 5

Met Gly Thr Trp Ile Leu Phe Ala Cys Leu Leu Gly Ala Ala Phe Ala
1               5                   10                  15

Met Pro Leu Pro Pro His Pro Gly His Pro Gly Tyr Ile Asn Phe Ser
            20                  25                  30

Tyr Glu Asn Ser His Ser Gln Ala Ile Asn Val Asp Arg Thr Ala Leu
        35                  40                  45

Val Leu Thr Pro Leu Lys Trp Tyr Gln Ser Ile Arg Pro Pro Tyr Pro
    50                  55                  60

Ser Tyr Gly Tyr Glu Pro Met Gly Gly Trp Leu His His Gln Ile Ile
65                  70                  75                  80

Pro Val Leu Ser Gln Gln His Pro Pro Thr His Thr Leu Gln Pro His
                85                  90                  95

His His Ile Pro Val Val Pro Ala Gln Gln Pro Val Ile Pro Gln Gln
            100                 105                 110

Pro Met Met Pro Val Pro Gly Gln His Ser Met Thr Pro Ile Gln His
        115                 120                 125

His Gln Pro Asn Leu Pro Pro Pro Ala Gln Gln Pro Tyr Gln Pro Gln
    130                 135                 140

Pro Val Gln Pro Gln Pro His Gln Pro Met Gln Pro Gln Pro Pro Val
145                 150                 155                 160

His Pro Met Gln Pro Leu Pro Pro Gln Pro Pro Leu Pro Pro Met Phe
                165                 170                 175

Pro Met Gln Pro Leu Pro Pro Met Leu Pro Asp Leu Thr Leu Glu Ala
            180                 185                 190

Trp Pro Ser Thr Asp Lys Thr Lys Arg Glu Glu Val Asp
        195                 200                 205


<210> SEQ ID NO 6
<211> LENGTH: 195
<212> TYPE: PRT
<213> ORGANISM: Rattus norvegicus

<400> SEQUENCE: 6

Met Gly Thr Trp Ile Leu Phe Ala Cys Leu Leu Gly Ala Ala Phe Ala
```

-continued

```
1               5                   10                  15

Met Pro Leu Pro Pro His Pro Gly Ser Pro Gly Tyr Ile Asn Leu Ser
            20                  25                  30

Tyr Glu Val Leu Thr Pro Leu Lys Trp Tyr Gln Ser Met Ile Arg Gln
        35                  40                  45

Pro His Pro Pro Ser His Thr Leu Gln Pro His His His Leu Pro Val
    50                  55                  60

Val Pro Ala Gln Gln Pro Val Ala Pro Gln Gln Pro Met Met Pro Val
65                  70                  75                  80

Pro Gly His His Ser Met Thr Pro Thr Gln His His Gln Pro Asn Ile
                85                  90                  95

Pro Pro Ser Ala Gln Gln Pro Phe Gln Gln Pro Phe Gln Pro Gln Ala
            100                 105                 110

Ile Pro Pro Gln Ser His Gln Pro Met Gln Pro Gln Ser Pro Leu His
        115                 120                 125

Pro Met Gln Pro Leu Ala Pro Gln Pro Pro Leu Pro Pro Leu Phe Ser
    130                 135                 140

Met Gln Pro Leu Ser Pro Ile Leu Pro Glu Leu Pro Leu Glu Ala Trp
145                 150                 155                 160

Pro Ala Thr Asp Lys Thr Lys Arg Glu Glu Val Ala Phe Ser Pro Met
                165                 170                 175

Lys Trp Tyr Gln Gly Thr Ala Arg His Pro Leu Asn Met Glu Thr Thr
            180                 185                 190

Thr Glu Lys
        195


<210> SEQ ID NO 7
<211> LENGTH: 210
<212> TYPE: PRT
<213> ORGANISM: Mus musculus

<400> SEQUENCE: 7

Met Gly Thr Trp Ile Leu Phe Ala Cys Leu Leu Gly Ala Ala Phe Ala
1               5                   10                  15

Met Pro Leu Pro Pro His Pro Gly Ser Pro Gly Tyr Ile Asn Leu Ser
            20                  25                  30

Tyr Glu Lys Ser His Ser Gln Ala Ile Asn Thr Asp Arg Thr Ala Leu
        35                  40                  45

Val Leu Thr Pro Leu Lys Trp Tyr Gln Ser Met Ile Arg Gln Pro Tyr
    50                  55                  60

Pro Ser Tyr Gly Tyr Glu Pro Met Gly Gly Trp Leu His His Gln Ile
65                  70                  75                  80

Ile Pro Val Leu Ser Gln Gln His Pro Pro Ser His Thr Leu Gln Pro
                85                  90                  95

His His His Leu Pro Val Val Pro Ala Gln Gln Pro Val Ala Pro Gln
            100                 105                 110

Gln Pro Met Met Pro Val Pro Gly His His Ser Met Thr Pro Thr Gln
        115                 120                 125

His His Gln Pro Asn Ile Pro Pro Ser Ala Gln Gln Pro Phe Gln Gln
    130                 135                 140

Pro Phe Gln Pro Gln Ala Ile Pro Pro Gln Ser His Gln Pro Met Gln
145                 150                 155                 160

Pro Gln Ser Pro Leu His Pro Met Gln Pro Leu Ala Pro Gln Pro Pro
                165                 170                 175
```

```
Leu Pro Pro Leu Phe Ser Met Gln Pro Leu Ser Pro Ile Leu Pro Glu
            180                 185                 190

Leu Pro Leu Glu Ala Trp Pro Ala Thr Asp Lys Thr Lys Arg Glu Glu
        195                 200                 205

Val Asp
    210


<210> SEQ ID NO 8
<211> LENGTH: 55
<212> TYPE: PRT
<213> ORGANISM: Sus scrofa

<400> SEQUENCE: 8

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Asn Met Ile Arg His
            20                  25                  30

Pro Ser Leu Leu Pro Asp Leu Leu Glu Ala Trp Pro Ala Thr Asp Lys
        35                  40                  45

Thr Lys Arg Glu Glu Val Asp
    50                  55


<210> SEQ ID NO 9
<211> LENGTH: 58
<212> TYPE: PRT
<213> ORGANISM: Homo sapiens

<400> SEQUENCE: 9

Met Pro Leu Pro Pro His Pro Gly His Pro Gly Tyr Ile Asn Phe Ser
1               5                   10                  15

Tyr Glu Val Leu Thr Pro Leu Lys Trp Tyr Gln Ser Ile Arg Pro Pro
            20                  25                  30

Pro Leu Pro Pro Met Leu Pro Asp Leu Thr Leu Glu Ala Trp Pro Ser
        35                  40                  45

Thr Asp Lys Thr Lys Arg Glu Glu Val Asp
    50                  55


<210> SEQ ID NO 10
<211> LENGTH: 32
<212> TYPE: PRT
<213> ORGANISM: Artificial
<220> FEATURE:
<223> OTHER INFORMATION: Amelogenin-derived polypeptide

<400> SEQUENCE: 10

Met Pro Leu Pro Ser Tyr Glu Val Leu Thr Pro Leu Lys Trp Pro Val
1               5                   10                  15

His Pro Met Gln Pro Ser Thr Asp Lys Thr Lys Arg Glu Glu Val Asp
            20                  25                  30


<210> SEQ ID NO 11
<211> LENGTH: 26
<212> TYPE: PRT
<213> ORGANISM: Artificial
<220> FEATURE:
<223> OTHER INFORMATION: Amelogenin-derived polypeptide

<400> SEQUENCE: 11
```

-continued

```
Met Pro Leu Pro Ser Tyr Glu Val Leu Thr Pro Leu Lys Trp Pro Ser
1               5                   10                  15

Thr Asp Lys Thr Lys Arg Glu Glu Val Asp
            20                  25
```

AMELOGENIN-CHITOSAN HYDROGEL FOR DENTIN HYPERSENSITIVITY

CROSS-REFERENCE TO RELATED APPLICATIONS

This application claims the benefit of U.S. provisional application Ser. No. 62/189,356 filed Jul. 7, 2015, the disclosure of which is hereby incorporated in its entirety by reference herein.

STATEMENT REGARDING FEDERALLY SPONSORED RESEARCH OR DEVELOPMENT

The invention was made with Government support under Contract No. (301)594-7703 awarded by the National Institute of Dental and Craniofacial Research. The Government has certain rights to the invention.

SEQUENCE LISTING

The text file SequenceListing_ST25.txt of size 14 KB created Sep. 21, 2016 filed herewith, is hereby incorporated by reference.

TECHNICAL FIELD

In at least one aspect, the present invention is related to the methods of reconstructing enamel.

BACKGROUND

Enamel is the exterior layer of the mammalian tooth. Dentin is the underlying calcified tissue, similar in composition to bone, that constitutes the bulk of the tooth structure. Dentin is secreted by the odontoblasts to form a large number of closely packed S-shaped dentinal tubules in a mineralized collagen matrix. Together with the overlying enamel, it provides resilience and rigidity to the tooth structure against masticatory and shearing forces. Exposure of dentinal tubules to the oral environment may occur due to several factors like dental caries, erosion, abrasion, attrition, failed restorations, cracked cusps and gingival recession. This can prompt a sharp acute pain response termed dentinal hypersensitivity explained by the increased dentinal tubular fluid flow, which activates the nerve fibers for pain. Currently, no clinically viable strategies are available to regrow an enamel-like tissue on a dentin substrate.

SUMMARY

In at least one embodiment, a method to regrow a protective layer over demineralized dentin is provided. The method includes a step of identifying a subject having exposed and/or demineralized dentin. The demineralized/exposed dentin is contacted with a remineralization composition that includes an amelogenin, a chitosan, water, and a sufficient amount of a pH adjusting component such that the composition has a pH greater than about 6.0 (e.g., about 6.5) such that enamel is regrown on the dentinal tubules. The present embodiment is a peptide-based biomimetic approach that uses a chitosan/amelogenin-derived peptide (i.e. LRAP, P26, and P32) hydrogel to regrow a protective layer over exposed dentin. Advantageously, the method restores the integrity of the tissue against future acid attacks thereby providing a treatment for dentinal hypersensitivity, root caries and cases of severe enamel loss associated with deep caries and dental erosion.

Advantageously, the present method enables the occlusion of dentinal tubules that were exposed due to physical and physiological forces acting within the oral cavity and/or the remineralization of demineralized collagen fibers with growth of a barrier layer of tightly adherent enamel-inspired crystalline material. This remineralization prevents any external stimulus from direct contact and activation of the nerve fibers for pain. The involvement of amelogenin-derived peptides (LRAP) modulates the apatite crystals to growth similar to the enamel crystal formation in vivo thus greatly increasing the strength and toughness of such material. The cell free method of the invention allows control of the product in terms of: the type of mineral, crystal orientation, and crystal morphology by controlling local pH, and ion concentrations (Mg,Ca,$PO_4$,F) and most importantly amelogenin and its derived concentration. Finally, since the composition used in the present embodiment is a cell free system, problems associated with contamination by cell component, which may cause severe immunological reactions, are avoided.

BRIEF DESCRIPTION OF THE DRAWINGS

FIG. 4C (inset) depicts heterogenous distribution of small needle-like crystallites closing the openings to the dentinal tubules in parts of the dentin surface. Peritubular (arrow) and intertubular (asterisk) dentin have also been shown in the images (A, B).

DETAILED DESCRIPTION

Figure 1:
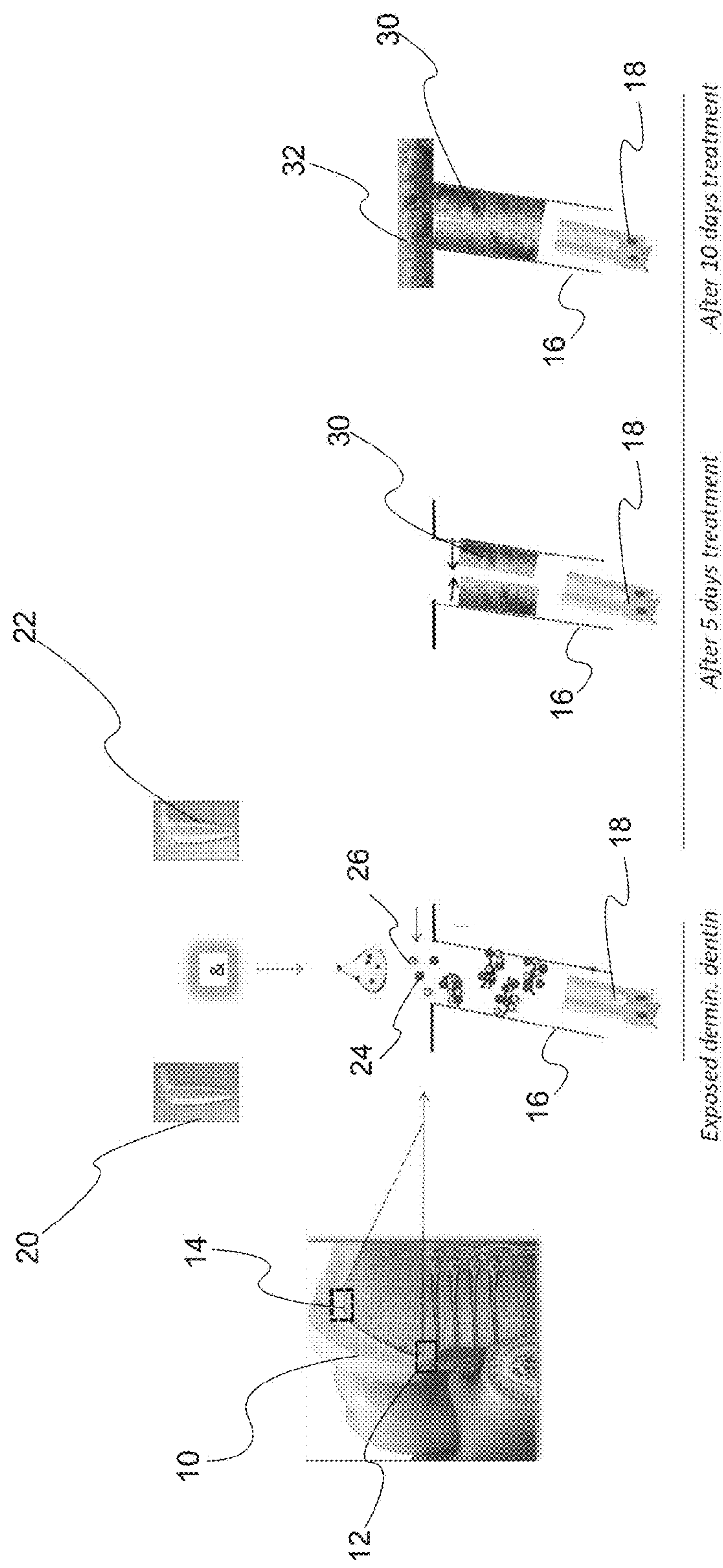
FIG. 1 provides a model for peptide-mediated dentin mineralization of a tooth having carious or non-carious cervical lesions.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of" and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. Where one of these three terms is used, the presently disclosed and claimed subject matter can include the use of either of the other two terms.

Throughout this application, where publications are referenced, the disclosures of these publications in their entireties are hereby incorporated by reference into this application to more fully describe the state of the art to which this invention pertains.

Abbreviations:

"CS" means chitosan.

"demin" means demineralized.

"HAP" means hydroxyapatite.

"LRAP" means leucine rich amelogenin polypeptide.

"P32" means peptide 32.

"P26" means peptide 26.

"XRD" means X-ray diffraction.

The term "hydrogel" refers to a gel in which the dispersion medium is water.

The term "subject" refers to a human or animal, including all mammals such as primates (particularly higher primates) having dental caries, early dental carious and erosive lesions as well as enamel defects resulting from genetic diseases.

The term "polypeptide" refers to a polymer of amino acids and its equivalent and does not refer to a specific length of the product; thus, peptides, oligopeptides and proteins are included within the definition of a polypeptide. This term also does not exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring.

The terms "sequence identity" or "identity" refers to a specified percentage of residues in two nucleic acid or amino acid sequences that are identical when aligned for maximum correspondence over a specified comparison window, as measured by sequence comparison algorithms or by visual inspection. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity.

The term "comparison window" refers to a segment of at least about 20 contiguous positions in which a sequence may be compared to a reference sequence of the same number of contiguous positions after the two sequences are aligned optimally. In a refinement, the comparison window is from 15 to 30 contiguous positions in which a sequence may be compared to a reference sequence of the same number of contiguous positions after the two sequences are aligned optimally. In another refinement, the comparison window is usually from about 50 to about 200 contiguous positions in which a sequence may be compared to a reference sequence of the same number of contiguous positions after the two sequences are aligned optimally.

The term "amelogenin" refers to the closely related polypeptides involved in the formation of enamel and isoforms thereof. Amelogenin is exemplified by SEQ ID NOs set forth in Table 1. In a refinement, this definition includes alternatively spliced isoforms such as LRAP (leucine rich amelogenin polypeptide). It should be appreciated that this definition includes polypeptides having 1 to 10 conservative substitutions of SEQ ID NOs: 1-9 as set forth below in more detail.

TABLE 1

Amelogenin Polypeptide Sequences

| | Species | Sequence |
|---|---|---|
| SEQ ID NO: 1 | *Sus scrofa* | MGTWILFACLLGAAFSMPLPPHPGHPGYINFSYEVLTPLKWYQNMIRHPYTSYGYEPMGGWLHHQIIPVVSQQTPQSHALQPHHHIPMVPAQQPGIPQQPMMPLPGQHSMTPTQHHQPNLPLPAQQPFQPQPVQPQPHQPLQPQSPMHPIQPLLPQPPLPPMFSMQSLLPDLPLEAWPATDKTKREEVD |
| SEQ ID NO: 2 | *Bos taurus* | FACLLGAAYSMPLPPHPGHPGYINFSYEVLTPLKWYQNMLRYPYPSYGYEPVGGWLHHQIIPVVSQQSPQNHALQPHHHNPMVPAQQPVVPQQPMMPVPGQHSMTPIQHHQPNLPLPAQQSFQPQPIQPQPHQPLQPQPPVHPIQRLPPQPPLPPIFPMQPLPPVLPDLPLEAWPATDKTKREE |
| SEQ ID NO: 3 | *Homo sapiens* | MGTWILFACLLGAAFAMPLPPHPGHPGYINFSYEVLTPLKWYQSIRPPYPSYGYEPMGGWLHHQIIPVLSQQHPPTHTLQPHHHIPVVPAQQPVIPQQPMMPVPGQHSMTPIQHHQPNLPPPAQQPYQPQPVQPQPHQPMQPQPPVHPMQPLPPQPPLPPMFPMQPLPPMLPDLTLEAWPSTDKTKREEVD |
| SEQ ID NO: 4 | *Pongo pygmaeus* | ACLLGAAFAMPLPPHPGHPGYINFSYENSHSQAINVDRTALVLTPLKWYQSIRPPYPSYGYEPMGGWLHHQIIPVLSQQHPPTHTLQPHHHIPVVPAQQPVIPQQPMMPVPGQHSMTPTQHHQPNLLPPAQQPYQPQPVQPQPHQPMQPQPPVHPMQPLPPQPPLPPMFPMQPLPPMLPDLTLEAWPSTDKTKREEVD |
| SEQ ID NO: 5 | *Pan troglodytes* | MGTWILFACLLGAAFAMPLPPHPGHPGYINFSYENSHSQAINVDRTALVLTPLKWYQSIRPPYPSYGYEPMGGWLHHQIIPVLSQQHPPTHTLQPHHHIPVVPAQQPVIPQQPMMPVPGQHSMTPIQHHQPNLPPPAQQPYQPQPVQPQPHQPMQPQPPVHPMQPLPPQPPLPPMFPMQPLPPMLPDLTLEAWPSTDKTKREEVD |
| SEQ ID NO: 6 | *Rattus norvegicus* | MGTWILFACLLGAAFAMPLPPHPGSPGYINLSYEVLTPLKWYQSMIRQPHPPSHTLQPHHHLPVVPAQQPVAPQQPMMPVPGHHSMTPTQHHQPNIPPSAQQPFQQPFQPQAIPPQSHQPMQPQSPLHPMQPLAPQPPLPPLFSMQPLSPILPELPLEAWPATDKTKREEVAFSPMKWYQGTARHPLNMETTTEK |
| SEQ ID NO: 7 | *Mus musculus* | MGTWILFACLLGAAFAMPLPPHPGSPGYINLSYEKSHSQAINTDRTALVLTPLKWYQSMIRQPYPSYGYEPMGGWLHHQIIPVLSQQHPPSHTLQPHHHLPVVPAQQPVAPQQPMMPVPGHHSMTPTQHHQPNIPPSAQQPFQQPFQPQAIPPQSHQPMQPQSPLHPMQPLAPQPPLPPLFSMQPLSPILPELPLEAWPATDKTKREEVD |
| SEQ ID NO: 8 | *Sus scrofa* | MPLPPHPGHPGYINFSYEVLTPLKWYQNMIRHPSLLPDLLEAWPATDKTKREEVD |
| SEQ ID NO: 9 | *Homo sapiens* (LRAP(+P) | MPLPPHPGHPGYINFSYEVLTPLKWYQSIRPPPLPPMLPDLTLEAWPSTDKTKREEVD |

In another variation, the term "amelogenin" also includes "amelogenin-derived polypeptides" having the ability to form enamel. Examples of amelogenin-derived polypeptides include the previously unknown polypeptides having SEQ ID NO: 10 and SEQ ID NO: 11 as set forth in Table 2 and variations of these polypeptides having conservative substitutions as set forth below in more detail.

TABLE 2

Artificial Amelogenin-derived polypeptides.

| | Description | Sequence |
|---|---|---|
| SEQ ID NO: 10 | Artificial (Peptide 32) | MPLPSYEVLTPLKWPVHPMQPSTDKTKREEVD |
| SEQ ID NO: 11 | Artificial (Peptide 26) | MPLPSYEVLTPLKWPSTDKTKREEVD |

In an embodiment of the present invention, a method to regrow a protective layer over exposed or demineralized dentin is provided. The method includes a step of identifying a subject having demineralized dentin (e.g., exposed dentinal tubules). The exposed or demineralized dentin is contacted with a remineralization composition that includes an amelogenin, a chitosan, water, and a sufficient amount of a pH adjusting component such that the composition has a pH greater than about 6.0 (e.g., 6.5) such that enamel is regrown on the exposed or demineralized dentin. Typically, the composition is allowed to air dry. The present method is advantageously used to remineralize dental lesions such as non-carious cervical lesions and class V caries.

In a variation, the method further includes a step contacting the demineralized dentin with a component selected from the group consisting of a calcium-containing compound, a phosphate containing compound, and combinations thereof. In some variations, the exposed/demineralized dentin is contacted with saliva or a solution including water and a component selected from the group consisting of electrolytes, mucus, glycoproteins, enzymes, antibacterial compounds, and combinations thereof.

In one refinement, the method also includes a step of contacting the substrate with a base (e.g., NaOH) for a first period of time. In a further refinement, the exposed or demineralized dentin is contacted with a component selected from the group consisting of calcium-containing compound, a phosphate containing compound, and combinations thereof for a second period of time. In still a further refinement, the exposed or demineralized dentin is contacted with saliva or a solution including water and a component selected from the group consisting of electrolytes, mucus, glycoproteins, enzymes, antibacterial compounds, and combinations thereof.

With reference to FIG. 1, a schematic illustration showing the remineralization of exposed dentin is provided. Tooth 10 is observed to have a cervical lesion 12 or class V caries 14 in which dentinal tubules 16 are exposed. Odontoblasts 18 are also depicted in FIG. 1. The exposed dentinal tubules are treated with the remineralization composition as either an amelogenin only peptide solution 20 or an amelogenin-chitosan gel 22. In either case, the composition also includes calcium ions 24 and phosphate ions 26 as set forth below in more detail. Peptide mediated agglomeration and nucleation of the calcium and phosphate ions occurs in region 30. After about 5 days occlusion of the dentinal tubules is observed as indicated by item number 30. After about 10 days, thin layer 32 of well-organized apatite crystals is regrown over the dentin.

Details of the remineralization compositions used in the methods set forth herein are provided in U.S. patent application Ser. No. 14/142,086 filed Dec. 27, 2013; the entire disclosure of which is hereby incorporated by reference. In particular, the chitosan has a formula described by a partially acetylated polysaccharide having formula I:

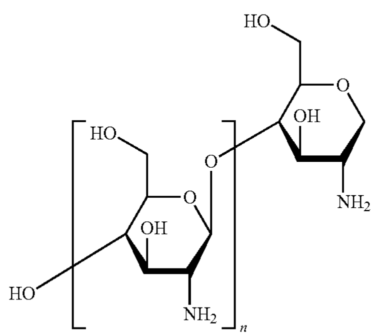

wherein n is from about 500 to 2500. In a refinement, the partially acetylated polysaccharide having formula I has a degree of acetylation less than about 35 percent. In a further refinement, the partially acetylated polysaccharide having formula I has a degree of acetylation from about 5 to 35 percent. The chitosan in general has a viscosity average molecular weight (Mv) from about 150,000 to 400,000 Daltons. In a refinement, the chitosan has an Mv from about 190,000 to 310,000 Daltons.

Examples of suitable amelogenins include, but are not limited to, porcine amelogenin rp172, mouse amelogenins, human amelogenins, etc., recombinant variations thereof, and isoforms thereof, and combinations thereof. Such isoforms include truncated amelogenin rP147 or an alternatively spliced isoform such as LRAP (leucine rich amelogenin polypeptide) having 59 amino acids. SEQ ID NOs: 1-9 provide specific examples of amelogenins. In a variation, the amelogenins used in the methods herein are polypeptides having an amino acid sequence that is at least 80 percent identical to the polypeptides forth as SEQ ID NOs: 1-9. In other refinements, the amelogenin used in the methods herein are polypeptides having an amino acid sequence that is at least, in order of increasing preference, 85%, 90%. 91%, 92%, 93%, 94%, 95%, 96%, 97%, 98%, 98.5% or 99% percent identical to the amino acid sequence set forth as SEQ ID NOs: 1-9. Thus, the present invention also encompasses the use of sequences having a degree of sequence identity with the SEQ ID NOs: 1-9. Herein, the term "sequence identity" means a polypeptide having a certain similarity with the subject amino acid sequence. The similar amino acid sequence should provide a polypeptide which retains the functional activity of the sequence in re-mineralizing exposed dentin and forming enamel.

In another variation, the amelogenins used in the methods herein are amelogenin-derived polypeptides having an amino acid sequence that is at least 80 percent identical to the polypeptides forth as SEQ ID NOs: 10-11. In other refinements, the amelogenins used in the methods herein are amelogenin-derived polypeptides having an amino acid sequence that is at least, in order of increasing preference, 85%, 90%. 91%, 92%, 93%, 94%, 95%, 96%, 97%, 98%, 98.5% or 99% percent identical to the amino acid sequence set forth as SEQ ID NOs: 1-9. These similar amino acid sequences should provide a polypeptide which retains the functional activity of the sequence in re-mineralizing exposed dentin and forming enamel. In still another refinement, a polynucleotide that encodes the amino acid sequences forth as SEQ ID NOs: 10-11 is also provided.

In a refinement, sequence identity comparisons are conducted as is well known in the art using sequence comparison computer programs that use algorithms to align two or more sequences using a scoring system that rewards alignment of identical or similar amino acids and penalizes substitutions of non-similar amino acids and gaps. Computer programs for carrying out alignments include, but are not limited to, BLASTP which is publicly available from the National Center for Biotechnology Information (www.ncbi.nlm.nih.gov/). These programs calculate percent sequence identity and report the determined value. It is preferred to use the default values when using such software for amino acid sequence alignments. BLASTP is preferred to determine amino acid sequence identity between the subject polypeptide sequences SEQ ID NOs: 1-11 and a candidate polypeptide sequence according to the present invention. Details of the BLASTP algorithm are set forth in D. W. Mount "Bioinformatics: Sequence and Genome Analysis," Cold Spring Harbor Press (2004). A particularly preferred set of parameters for the BLASTP alignment includes a Blossum 62 scoring matrix with a gap penalty of 11, a gap extend penalty of 1, and conditional adjustments set to conditional compositional score matrix adjustment.

Other preferred parameters for the BLASTP alignment are an expected threshold of 10 and a word size of 3.

In other variations, the amelogenins (including the amelogenin-derived polypeptides), in particular the polypeptides, described by SEQ ID NOs: 1-11, include deletions, insertions or substitutions of amino acid residues which result in a functionally equivalent protein. Preferably, the substitutions are conservative being similar with respect to polarity, charge, solubility, hydrophobicity, hydrophiliticity, and/or the amphipathic nature of the residues, while preserving the functionality of forming enamel. Conservative substitutions that may be made are, for example, substitutions between aliphatic amino acids (alanine, valine, leucine, isoleucine), polar amino acids (glutamine, asparagine, serine, threonine), acidic amino acids (glutamic acid and aspartic acid), basic amino acids (arginine, lysine and histidine), aromatic amino acids (phenylalanine, tryptophan and tyrosine), large amino acids (phenylalanine and tryptophan), small amino acids (glycine, alanine) and hydroxyl amino acids (serine, threonine). In a refinement, the amelogenins include polypeptides having 1 to 10 (i.e., 1, 2, 3, 4, 5, 6, 7, 8, 9, or 10) conservative substitutions of SEQ ID NOs: 1-11. In another refinement, the amelogenins include polypeptides having 1 to 5 conservative substitutions of SEQ ID NOs: 1-11.

Typically, the amelogenin is present in an amount from about 0.02 percent to about 0.4 percent of the total weight of the first composition and the chitosan is present in an amount from about 0.2 to about 3 percent of the total weight of the first composition with the balance being water In a variation, the remineralization composition also includes a calcium-containing compound (e.g., $Ca_3(PO_4)_2$, $CaCl_2$) that provides calcium ions when dissolved in water. In a further refinement, the remineralization composition can further include a phosphate-containing compound that provides phosphate and/or hydrogen phosphate ions when dissolved in water. Examples of such phosphate-containing compound include, but are not limited to, $Na_2HPO_4$ which provides hydrogen phosphate ions ($HPO_4^{2-}$). Typically, the amount of the phosphate-containing compound is present in an amount from about 0.01 percent to about 0.2 percent of the total weight of the remineralization composition. The pH of the remineralization composition is set to a pH equal to or greater than 6.0. A base such as NaOH may be used to adjust the pH. In one variation, the remineralization composition is advantageously a hydrogel that is useful for re-construction of enamel while inhibiting bacterial growth.

In a variation, the remineralization composition includes an amelogenin, chitosan, a calcium-containing compound that provides calcium ion when dissolved in water (e.g., $CaCl_2$), a phosphate-containing compound (e.g., $Na_2HPO_4$) that provides phosphate ions and/or hydrogen phosphate ions when dissolved in water, and water. Examples of suitable amelogenins are set forth above. Typically, the amelogenin is present in an amount from about 0.02 percent to about 0.2 percent of the total weight of the second composition and the chitosan is present in an amount from about 0.2 to about 3 percent of the total weight of the second composition, and the calcium containing compound is present in an amount from about 0.01 percent to about 0.2 percent of the total weight of the second composition with the balance being water. The details regarding the chitosan are also set forth above. In a refinement, the remineralization composition further includes a compound such as $Na_2HPO_4$ providing hydrogen phosphate ions ($HPO_4^{2-}$). Typically, the amount of the compound providing phosphate ions is present in an amount from about 0.01 percent to about 0.2 percent of the total weight of the remineralization composition. The pH of the second composition is set to a pH equal to or greater than 6.0 (e.g., about 6.5). A base such as NaOH may be used to adjust the pH to a value of 6.0 or greater. The remineralization composition is advantageously a hydrogel that is useful for re-construction of enamel while inhibiting bacterial growth.

The remineralization composition is advantageously used to re-construct enamel by contacting an exposed dentin substrate (e.g., a tooth) with the composition and then allowing the composition to air dry. The dentin coated substrate is then optionally rinsed and then contacted with saliva for an extended period of time (>24 hours).

In one or more variations of the remineralization composition, additional protein components are included. Examples of such additional components include, but are not limited to, enamelin, ameloblastin, enamel proteases, chitosanolytic enzymes, and combinations thereof. Suitable enamel proteases include, but are not limited to, Kallikrein-related peptidase 4 (KLK-4) and matrix metalloproteinase-20 (MMP-20). In a refinement, these additional components are individually or collectively present in an amount from about 0.005 percent to about 0.1 percent of the total weight of the first composition.

In another embodiment, a method for remineralizing a variety of dental lesions with remineralization compositions that include a polypeptide having SEQ ID NO: 1 or 2 is provided. Advantageously, this method can remineralize dental caries, early dental carious and erosive lesions, and enamel defects in addition to lesions having exposed dentin. The method includes a step of identifying a subject having a dental lesion and then contacting the dental lesion with a remineralization composition. The method also includes a step of allowing the remineralization composition to air dry. Characteristically, the remineralization composition includes a polypeptide comprising the amino acid sequence of SEQ ID NO: 10 or SEQ ID NO: 11, with up to 10 conservative amino acid substitutions (or identity with) as set forth above. The remineralization composition also includes an optional chitosan, water (balance), a sufficient amount of a pH adjusting component such that the composition has a pH greater than about 6.0. The details of the chitosan are set forth above. Advantageously, enamel is regrown on the dental lesions.

Additional details of the remineralization composition for this embodiment are provided in U.S. patent application Ser. No. 14/142,086 filed Dec. 27, 2013 with the peptides replacing the amelogenin in that reference. In particular, the remineralization composition can include a calcium-containing compound that provides calcium ion when dissolved in water and a phosphate containing compound that provides phosphate ions when dissolved in water. In one refinement, the method also includes a step of contacting the dental lesion with a base (e.g., NaOH) for a first period of time. In a further refinement, the dental lesion is contacted with a component selected from the group consisting of calcium-containing compound, a phosphate containing compound, and combinations thereof for a second period of time. In still a further refinement, the dental lesion is contacted with saliva or an aqueous solution that includes water and a component selected from the group consisting of electrolytes, mucus, glycoproteins, enzymes, antibacterial compounds, and combinations thereof. In a refinement, these additional components are individually or collectively present in an amount from about 0.005 percent to about 0.1 percent of the total weight of the aqueous solution.

The composition and methods of the invention are further illustrated by the following examples. These are provided by way of illustration and are not intended in any way to limit the scope of the invention.

Polypeptide Design

Figure 2:
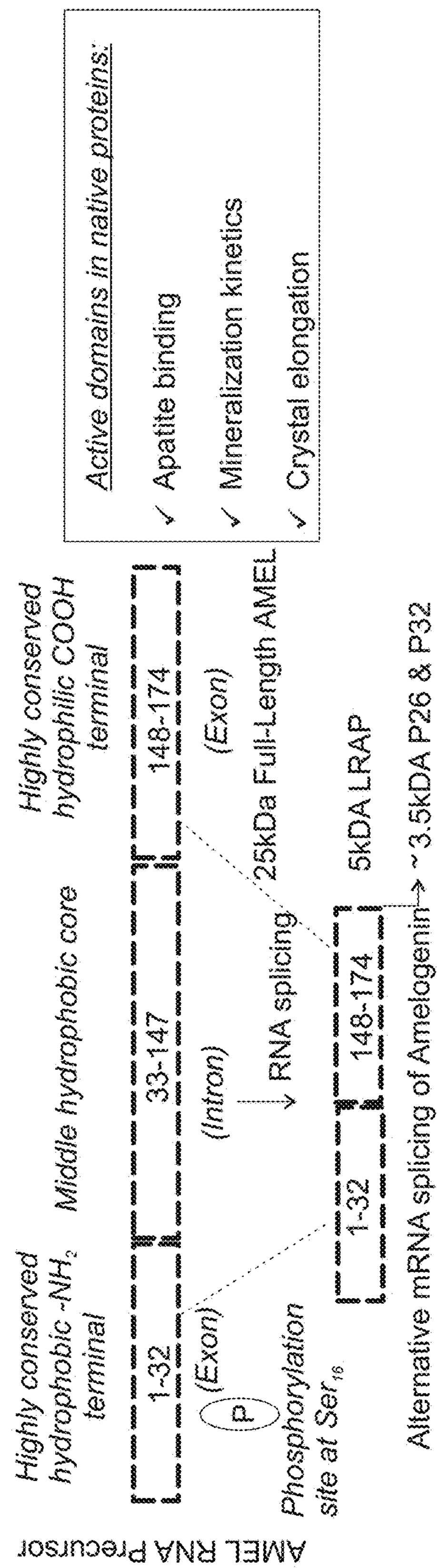
FIG. 2 provides a rationale for the design of amelogenin-inspired peptides from full-length amelogenin.
Figure 3A:
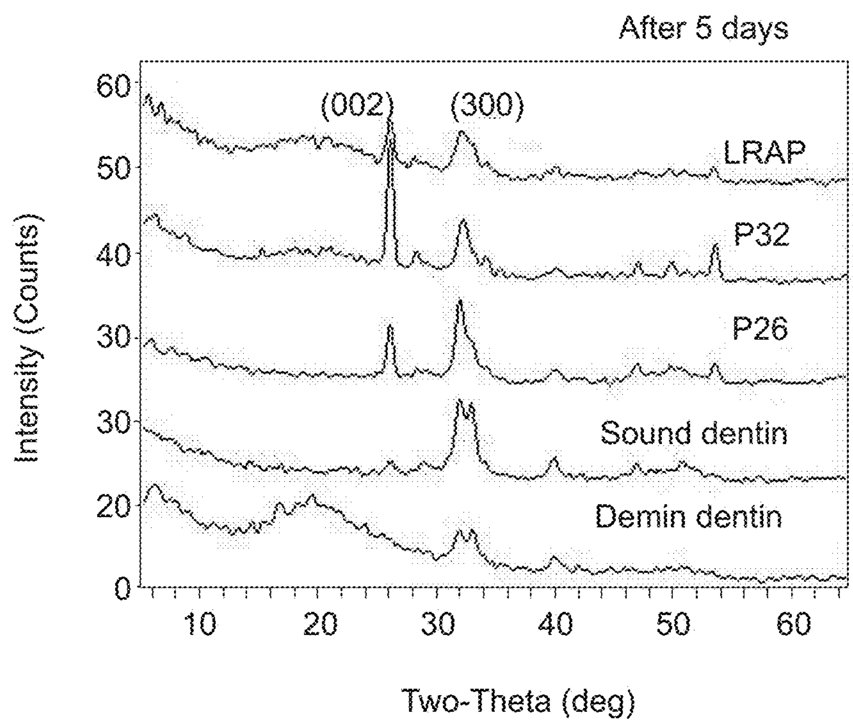
FIGS. 3A, 3B, 3C and 3D provide 4 XRD patterns of dentin slices treated with peptide only (A, B) and peptide-chitosan hydrogel (C, D) in artificial saliva for 5 and 10 days.
Figure 3B:
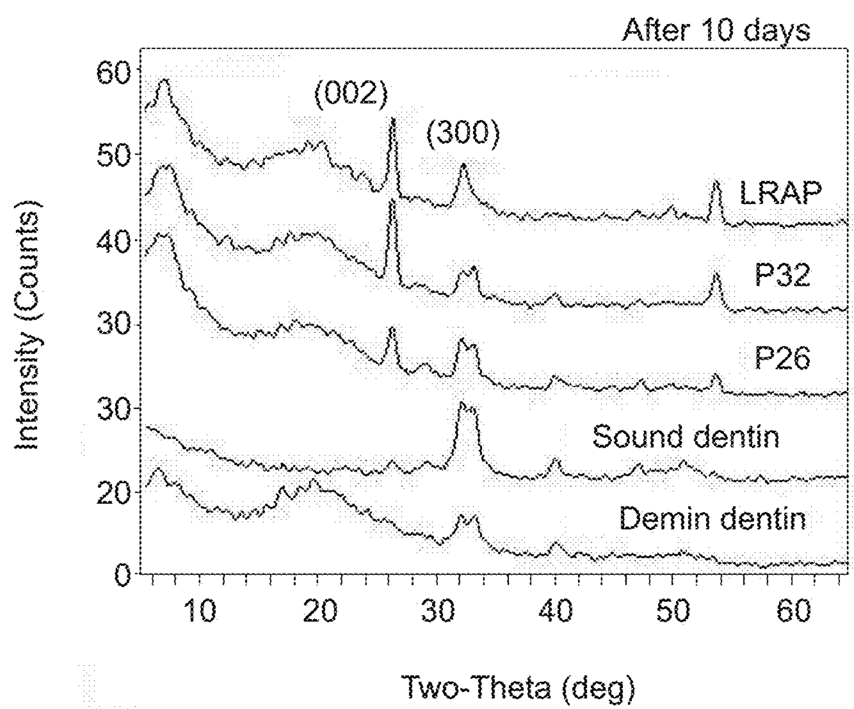
Figure 3C:
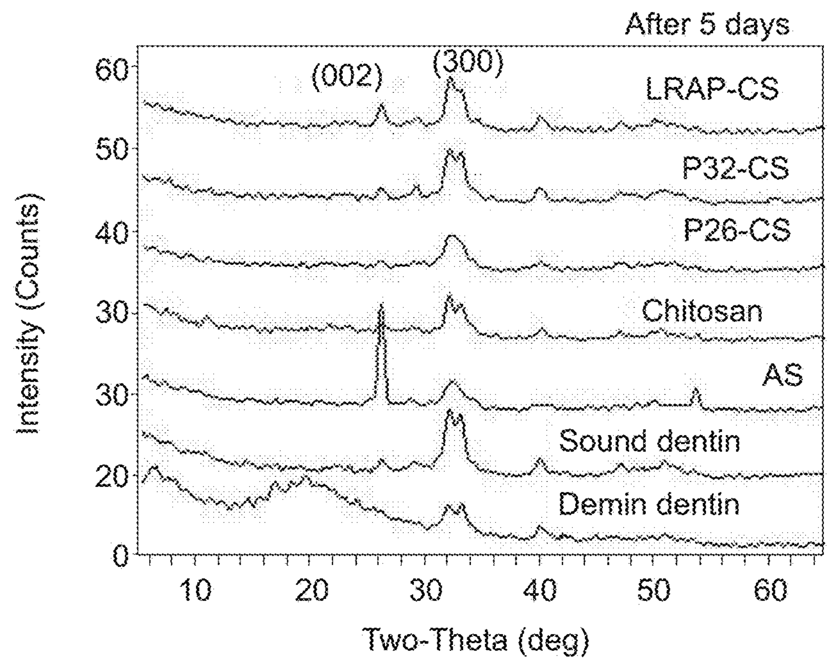
Figure 3D:
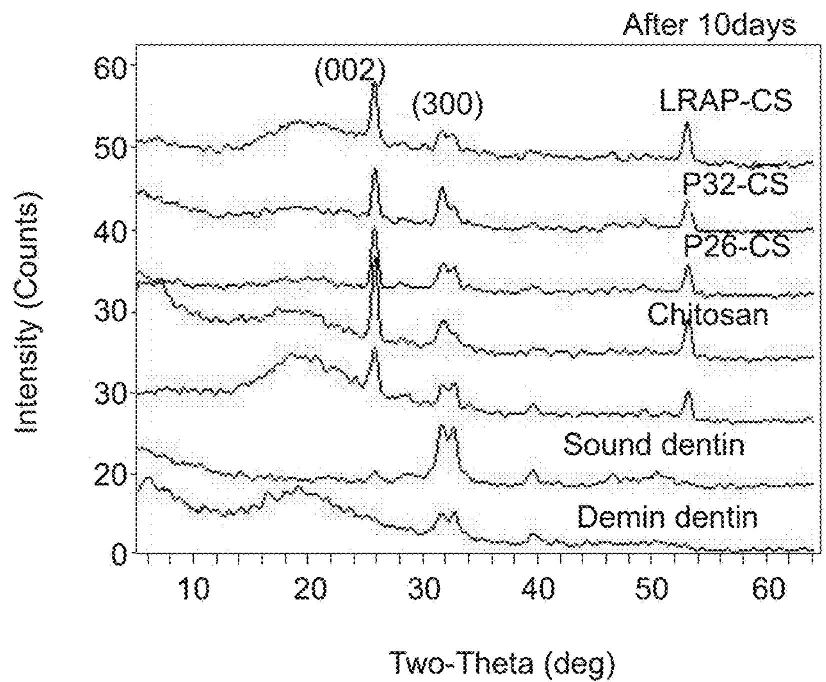

As illustrated in FIG. 2, the polypeptides having the amino acid sequence with SEQ ID NO: 10 and SEQ ID NO: 11 were inspired peptides as potential biomimetic regrowth strategies based on a critical understanding of the apatite binding and mineralization promoting domains of the native protein. The amino acid sequences SEQ ID NO: 10 and SEQ ID NO: 11 were synthesized by Chempeptide Limited, Shanghai, China. The amino acid SEQ ID NO: 11 retains the last 12 mers of the amelogenin C-terminus and includes about 50% of the charged residues of the full-length amelogenin. The close proximity of the hydrophilic C-terminus of amelogenin to the HAP surface has been directly implicated in mediating crystal nucleation and growth processes through a highly specific protein-crystal interaction. The 14 amino acid residues from the N-terminus (residues 1-4 and 16-25) with a phosphorylated Serine at the N-terminal were preserved. It has been shown through in vitro mineralization studies that the role of the N-terminal (+P) is to regulate crystal shape and stabilize ACP formation, thus playing a vital role in crystal morphology and apatite phase transition. For the amino acid sequence having SEQ ID NO: 10, two polyproline repeat regions (PXX/PXQ) were retained from the middle hydrophobic core of native amelogenin to observe whether addition of proline repeat length to the C-terminus would promote crystal elongation and growth as suggested in previous literature.

Treatment of a Tooth with the Remineralization Composition

Human third molars were sectioned transversally into 2 mm thick slices at the mid-coronal region of the tooth. A window of sound dentin measuring 2×2 mm each was delineated by applying two coats of acid-resistant nail varnish on the tooth surfaces. To mimic carious lesions, the samples were immersed in a demineralizing solution (pH 4.6, 30 ml) at 37° C. for 3 days. Twenty μl of peptide only (LRAP, P32, P26) and peptide-chitosan hydrogel (200 μg/ml) were applied separately on the demineralized windows (2 applications: Days 1 & 5) and the tooth slices were immersed in artificial saliva (pH 7, 5 ml) at 37° C. for 5 and 10 days. The artificial saliva includes 1.2 mM $Ca^{2+}$, 0.2 mM $Mg^{2+}$ 0.7 mM $H_2PO_4^-$, 16 mM KCl, 4.5 mM $NH_4Cl$ and 50 mM Hepes in water. The artificial saliva solution (5 ml) was changed daily from days 1-10.

Characterization of the Remineralization

FIG. 3 provides XRD patterns of the demineralized dentin, sound dentin, control samples (treated in artificial saliva and chitosan only), peptide only (A, B) and peptide chitosan hydrogel (C, D) treated dentin slices after being immersed in artificial saliva for 5 and 10 days.

Figure 4A:
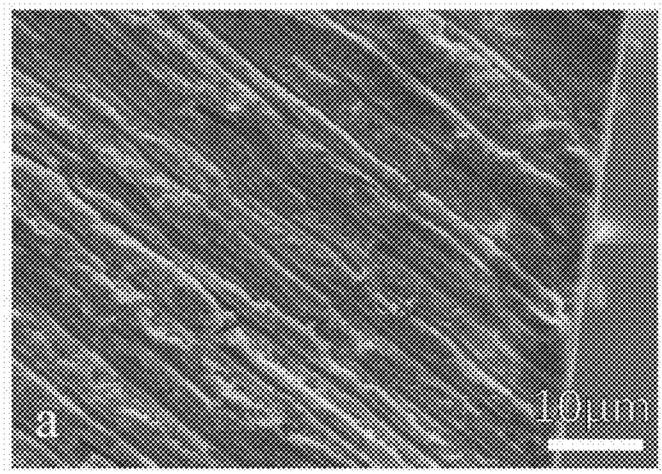
FIGS. 4A, 4B, and 4C provide SEM images showing the open ended dentinal tubules in healthy dentin (A), widened tubules in 3 day demineralized dentin (B) and chitosan gel treated dentin for 10 days (positive control) (C).
Figure 4B:
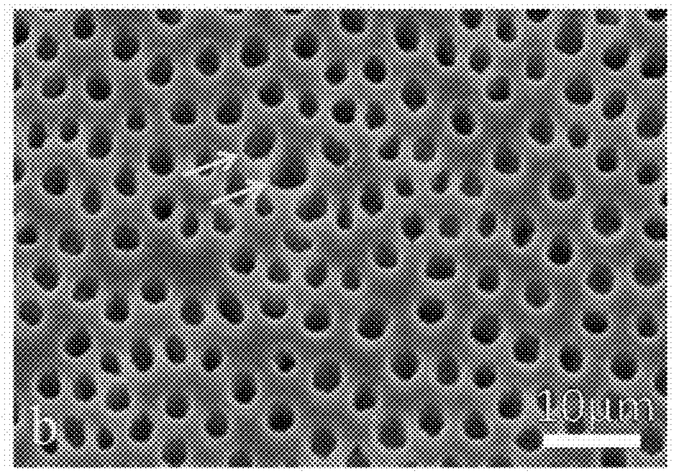
Figure 4C:
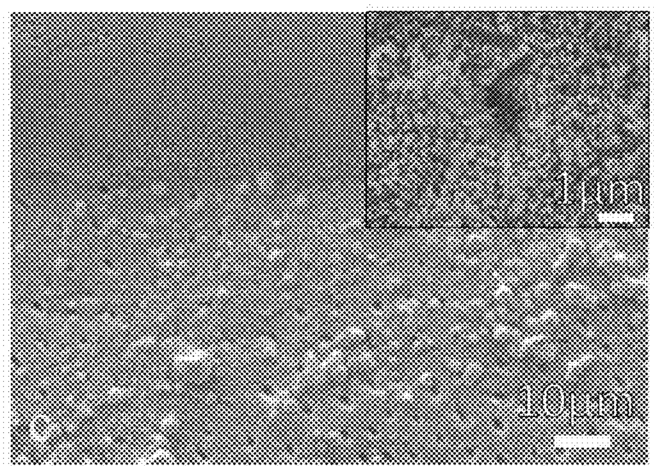

FIGS. 4A, 4B, and 4C provide SEM images showing the open ended dentinal tubules in healthy dentin (A), widened tubules in 3 day demineralized dentin (B) and chitosan gel treated dentin for 10 days (positive control) (C). FIG. 4C (inset) depicts heterogenous distribution of small needle-like crystallites closing the openings to the dentinal tubules in parts of the dentin surface. Peritubular (arrow) and intertubular (asterisk) dentin have also been shown in the images (A, B).

Figure 5A:
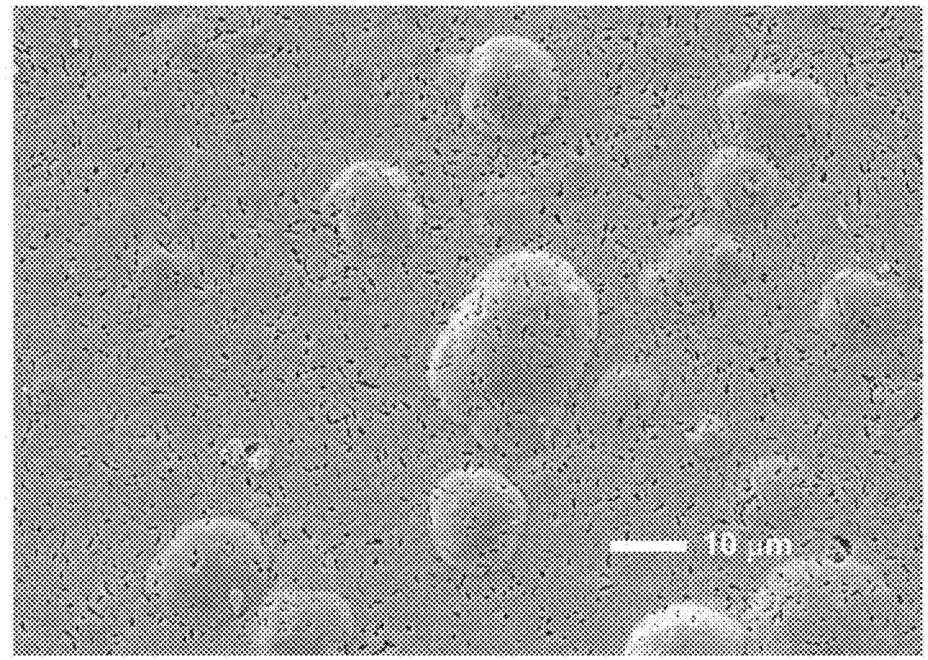
FIGS. 5A and 5B provide SEM images of the remineralized dentin slices after 5 days of treatment with LRAP (200 μg/ml).
Figure 5B:
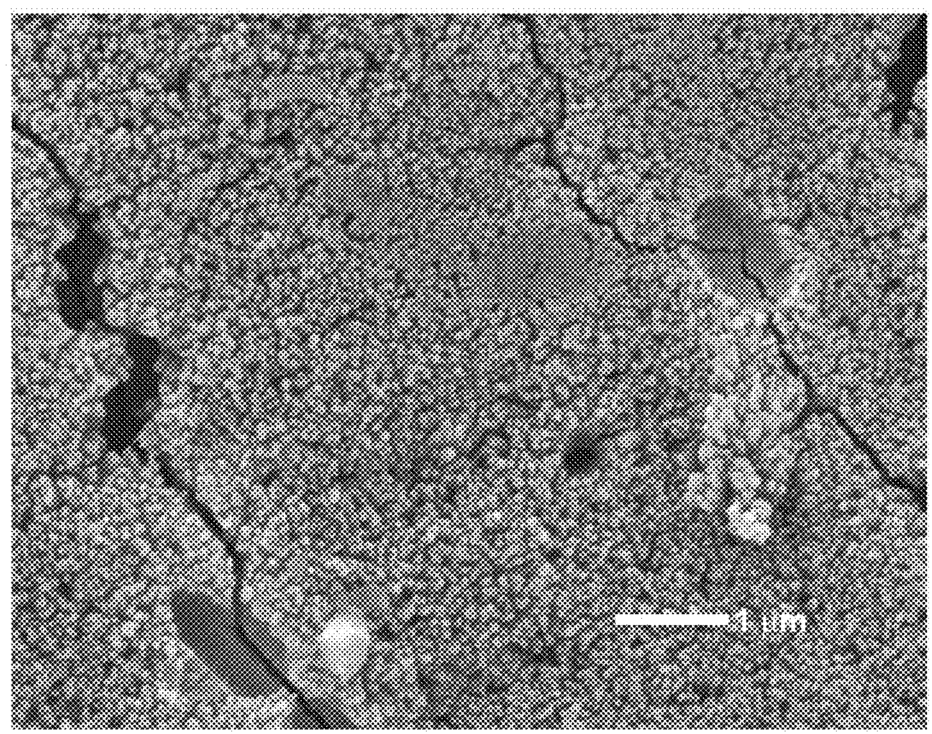
Figure 6A:
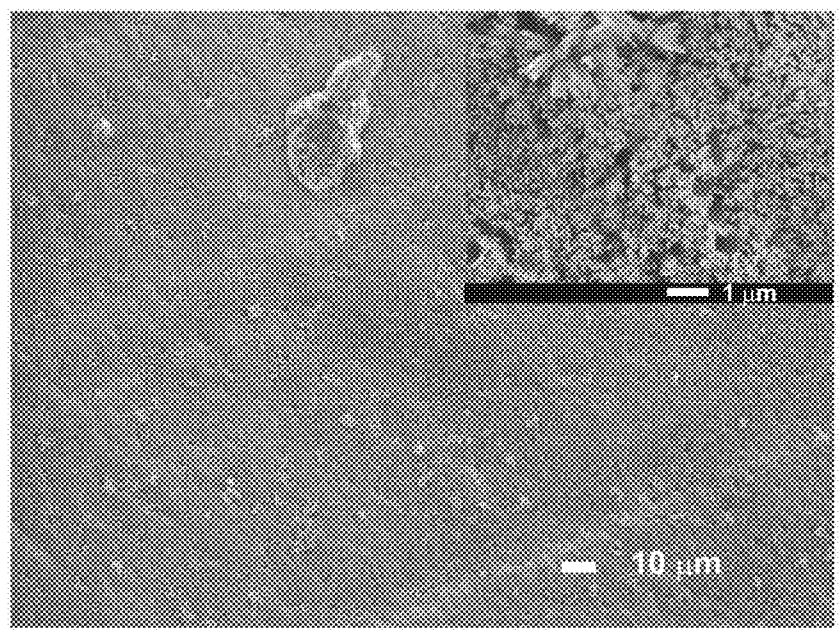
FIGS. 6A and 6B provide SEM images of the remineralized dentin slices after 5 days of treatment with polypeptide P32 (200 μg/ml).
Figure 6B:
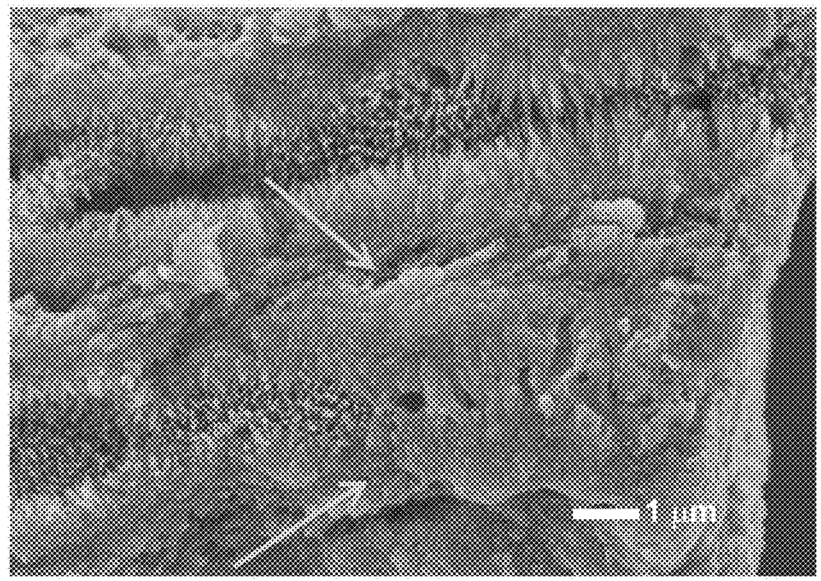
Figure 7A:
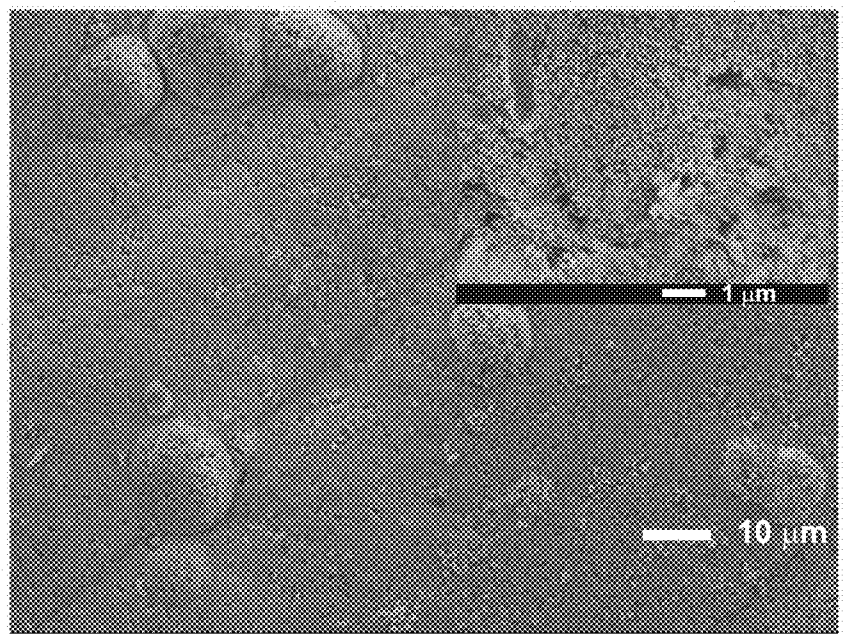
FIGS. 7A and 7B provide SEM images of the remineralized dentin slices after 5 days of treatment with polypeptide P26 (200 μg/ml).
Figure 7B:
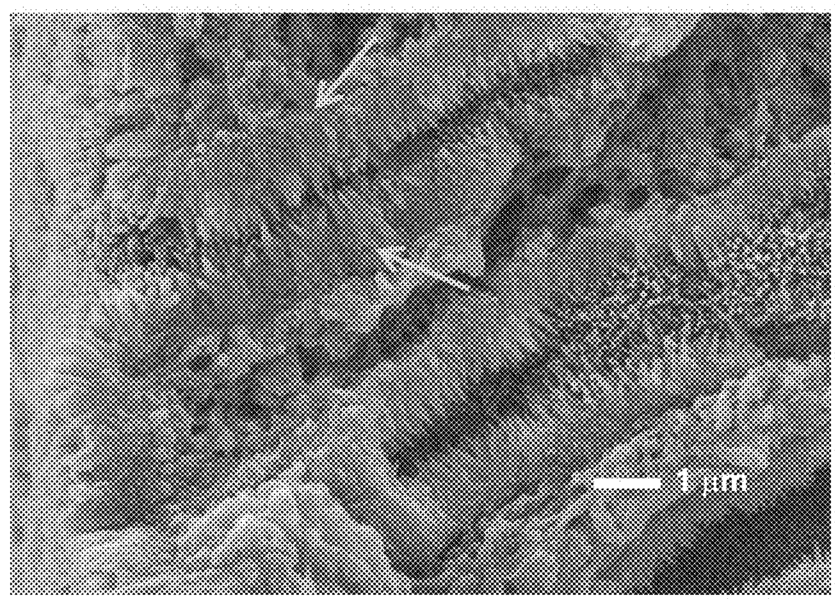

FIGS. 5A and 5B provide SEM images of the remineralized dentin slices after 5 days of treatment with LRAP. FIGS. 6A and 6B provides SEM images of the remineralized dentin slices after 5 days of treatment with polypeptide P32. FIGS. 7A and 7B provides SEM images of the remineralized dentin slices after 5 days of treatment with polypeptide P26. Needle-like HAP crystals densely are observed to cover the entire surface of demineralized dentin with complete occlusion of the dentinal tubules. The smaller images are enlarged details and cross-sections of the dentin slices.

Figure 8A:
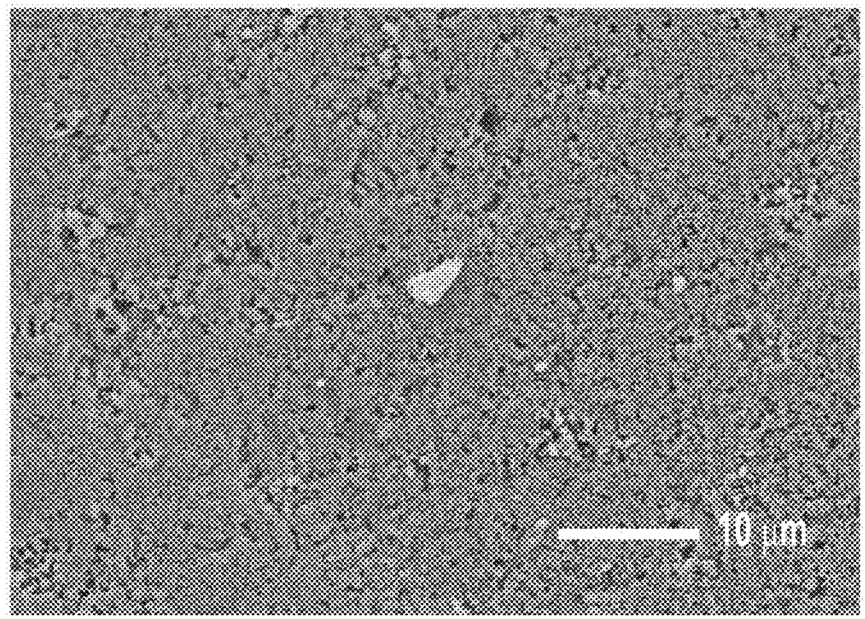
FIGS. 8A and 8B provide SEM images of the remineralized dentin slices after 10 days of treatment with LRAP (200 μg/ml).
Figure 8B:
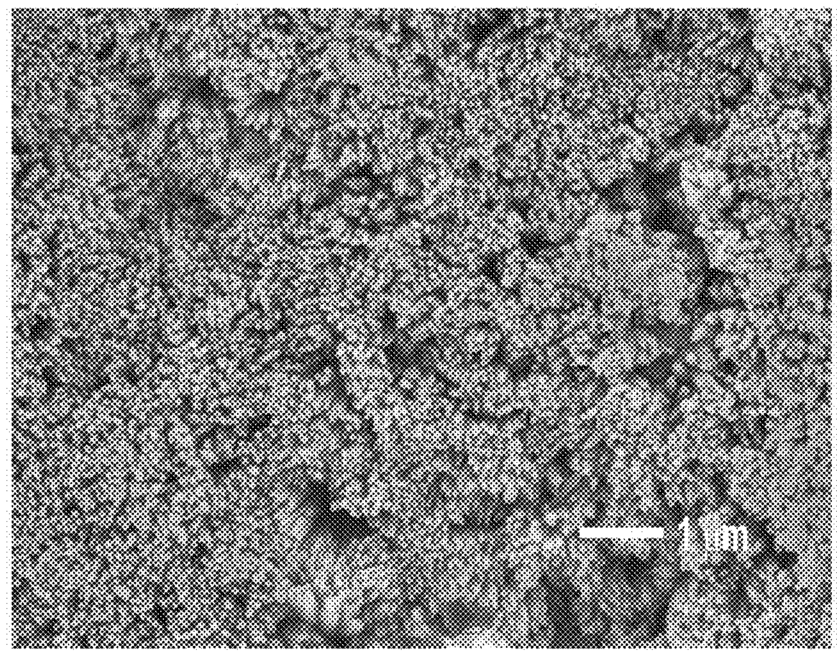
Figure 9A:
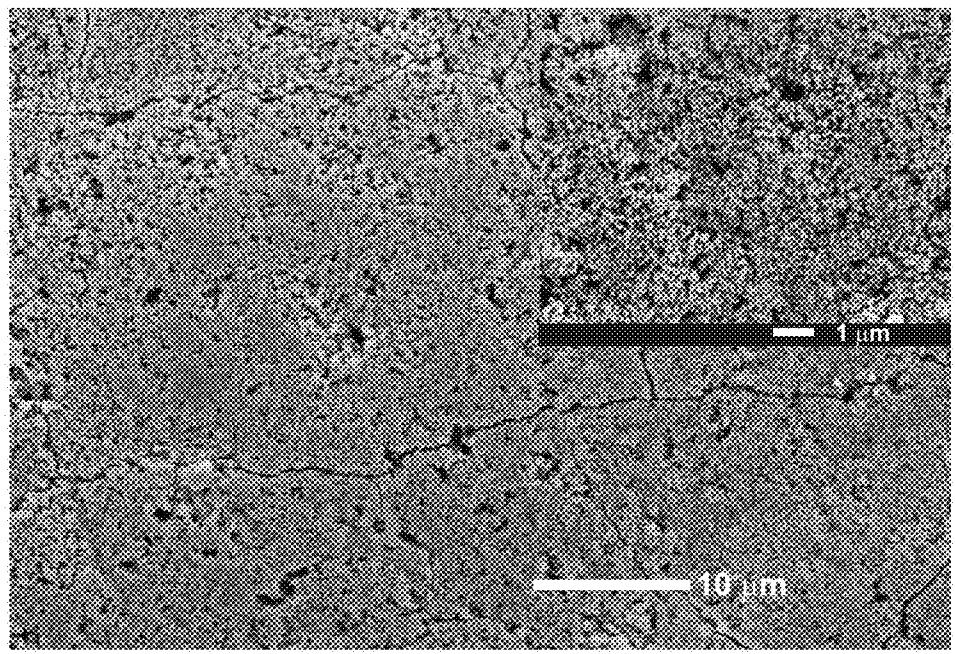
FIGS. 9A and 9B provide SEM images of the remineralized dentin slices after 10 days of treatment with polypeptide P32 (200 μg/ml).
Figure 9B:
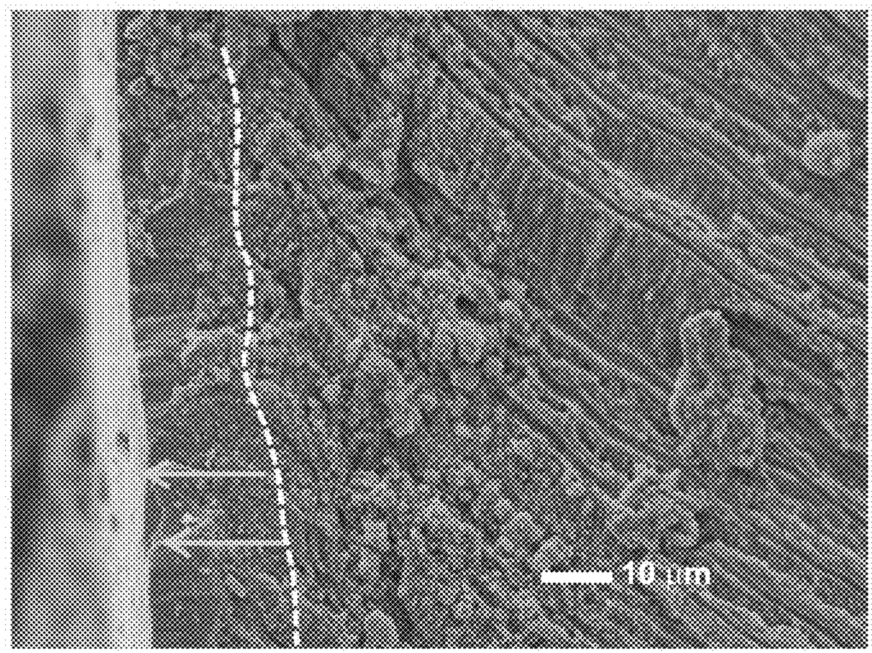
Figure 10A:
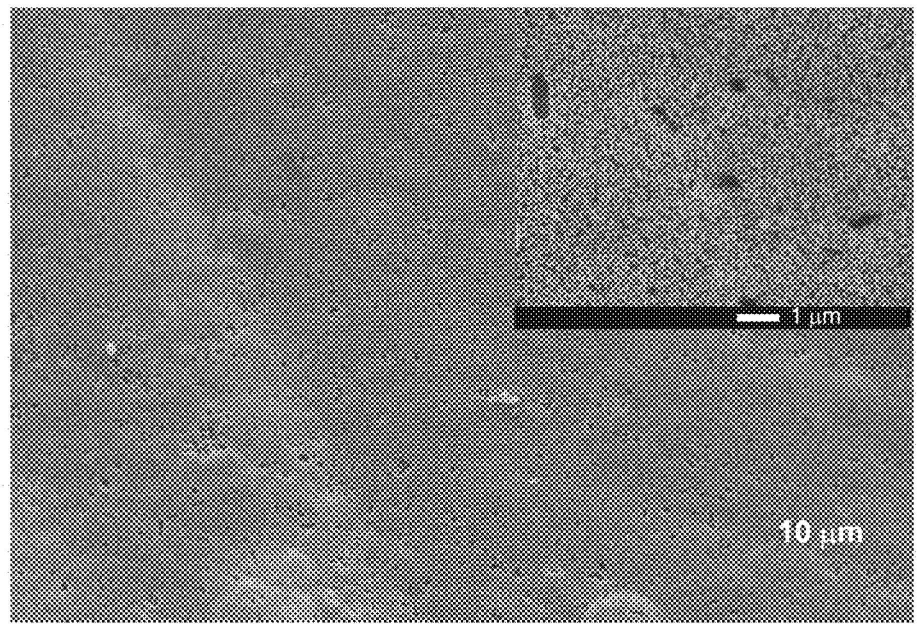
FIGS. 10A and 10B provide SEM images of the remineralized dentin slices after 10 days of treatment with polypeptide P26 (200 μg/ml).
Figure 10B:
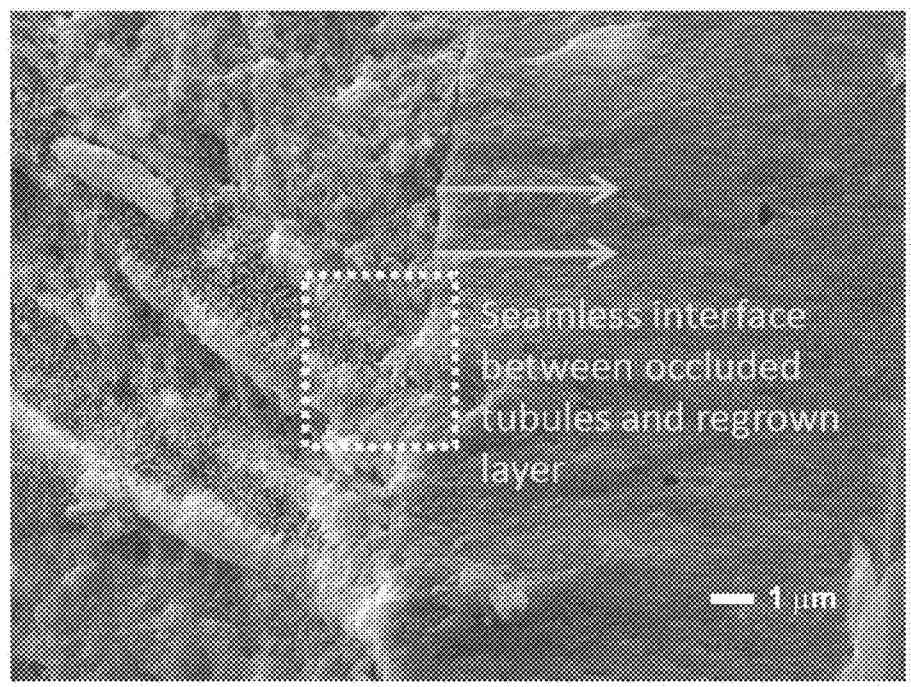

FIGS. 8A and 8B provide SEM images of the remineralized dentin slices after 10 days of treatment with LRAP. FIGS. 9A and 9B provides SEM images of the remineralized dentin slices after 10 days of treatment with polypeptide P32. FIGS. 10A and 10B provide SEM images of the remineralized dentin slices after 10 days of treatment with polypeptide P26. A well-organized newly grown layer was observed forming a robust interface with underlying native dentin. Apatite crystals grew from the walls of the dentinal tubules up to the dentin surface.

Figure 11:
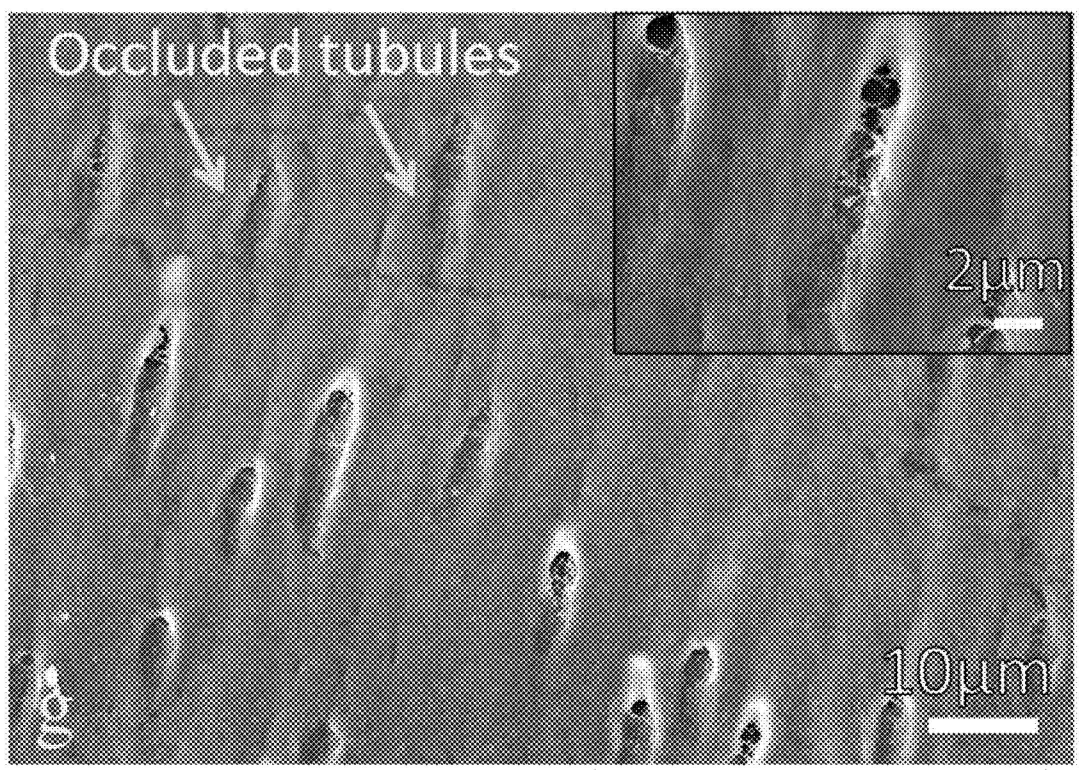
FIG. 11 provides SEM images of the remineralized dentin slices after 5 days of treatment with peptide-chitosan hydrogel LRAP-CS (200 μg/ml).
Figure 12:
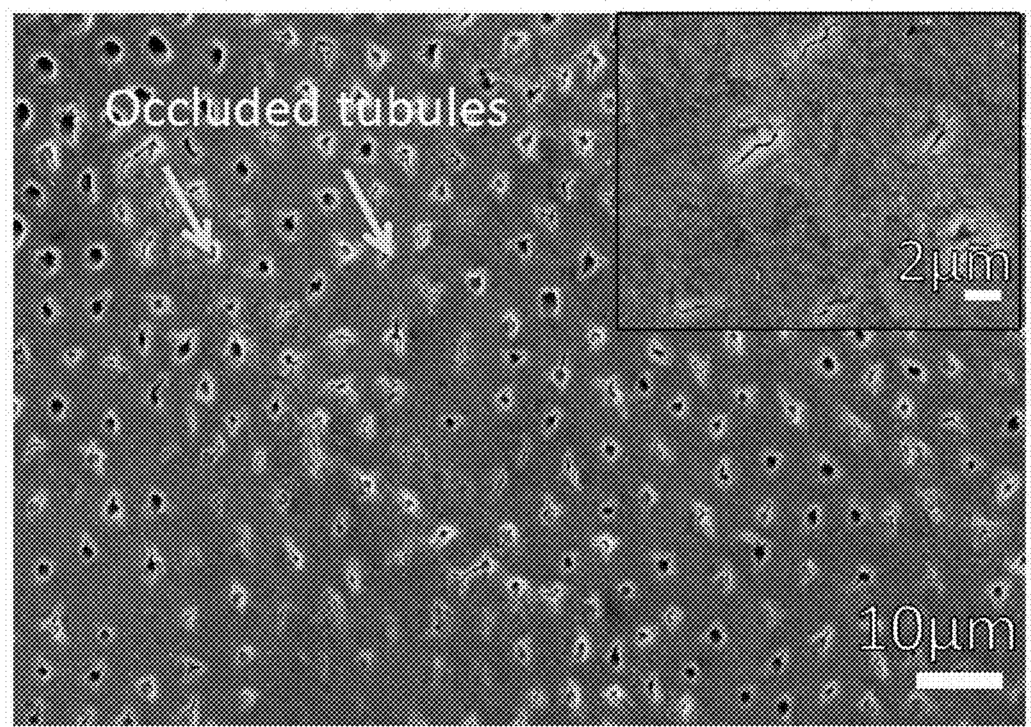
FIG. 12 provides SEM images of the remineralized dentin slices after 5 days of treatment with peptide-chitosan hydrogel P32-CS (200 μg/ml).
Figure 13:
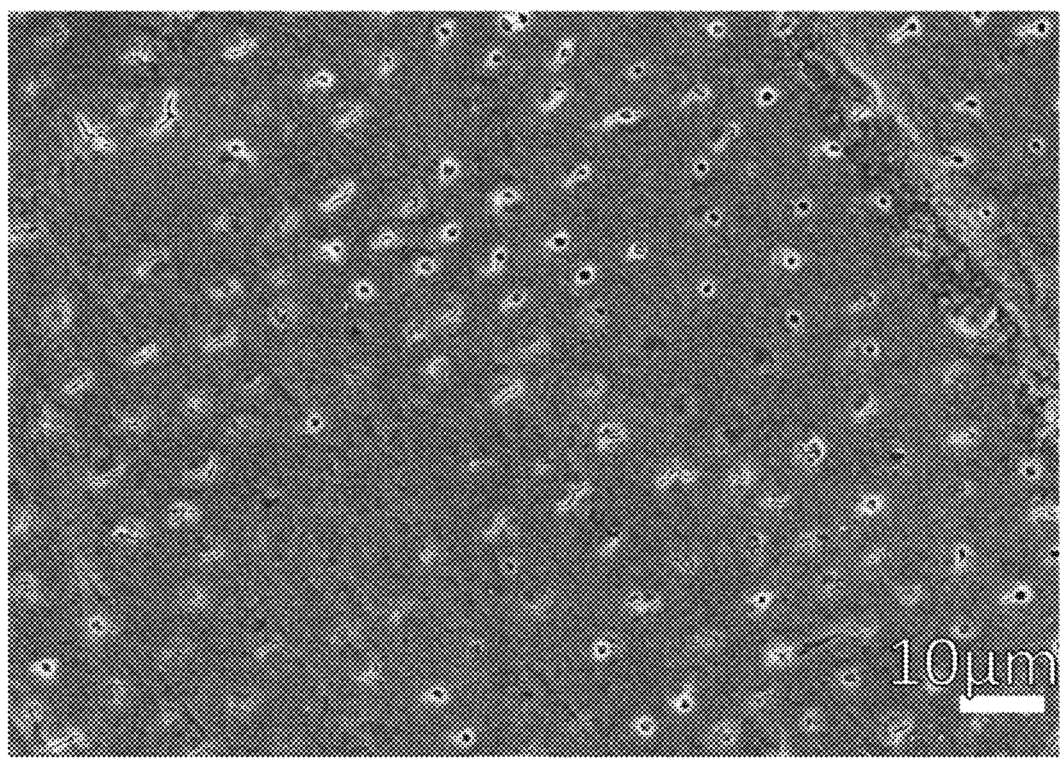
FIG. 13 provides SEM images of the remineralized dentin slices after 5 days of treatment with peptide-chitosan hydrogel P26-CS (200 μg/ml).
Figure 14A:
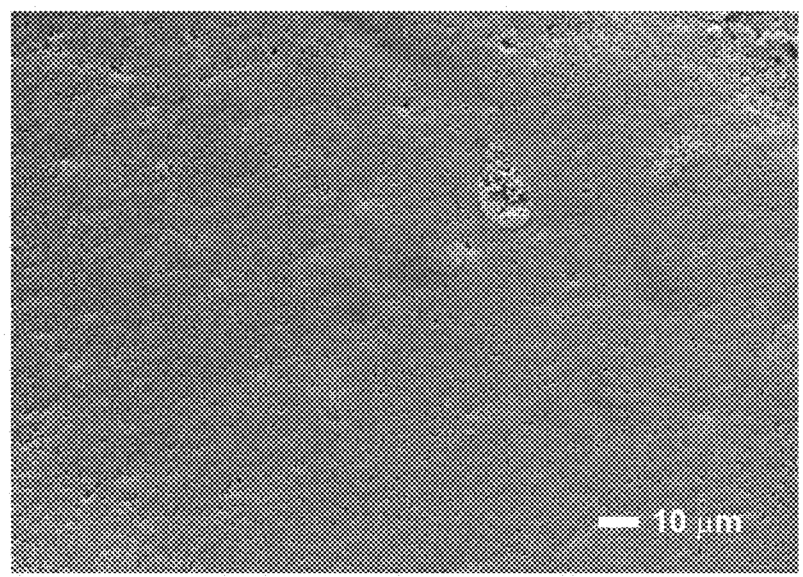
FIGS. 14A and 14B provide SEM images of the remineralized dentin slices after 10 days of treatment with peptide-chitosan hydrogel LRAP-CS (200 μg/ml).
Figure 14B:
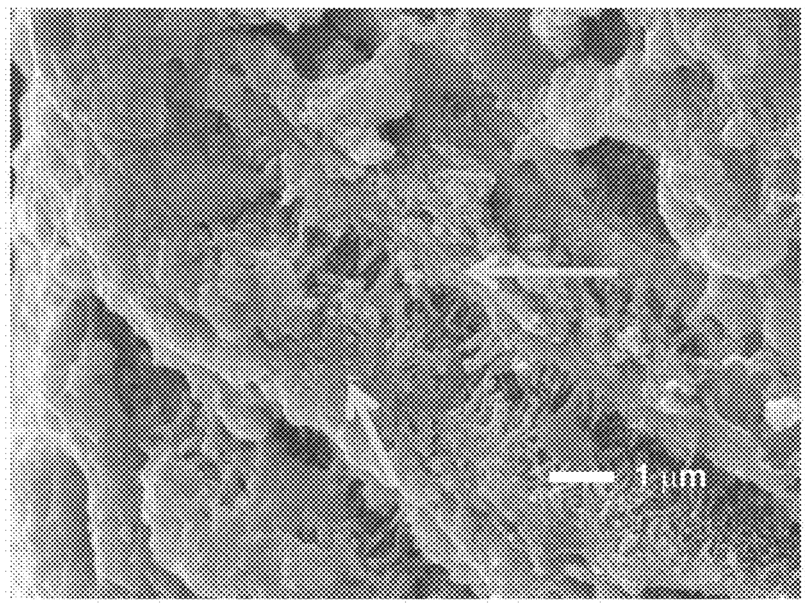
Figure 15A:
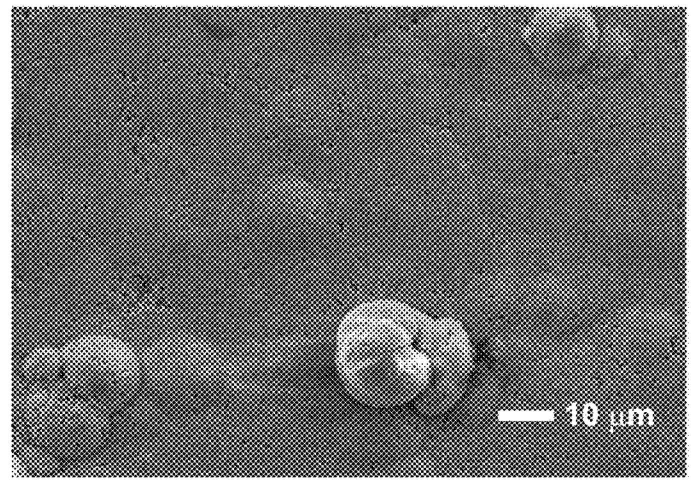
FIGS. 15A and 15B provide SEM images of the remineralized dentin slices after 10 days of treatment with peptide-chitosan hydrogel P32-CS (200 μg/ml). Areas of transition have been shown via dotted arrows as the mineralization advances from the occlusion of the tubules to the regeneration of enamel-like apatitic crystallites on the dentin surface.
Figure 15B:
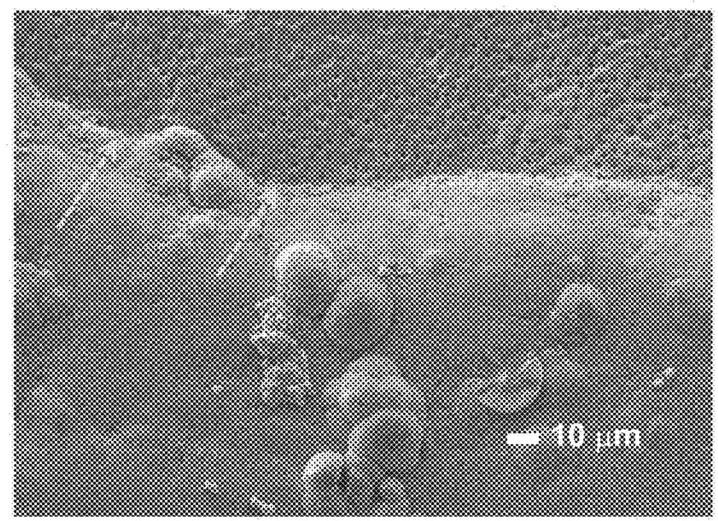
Figure 16A:
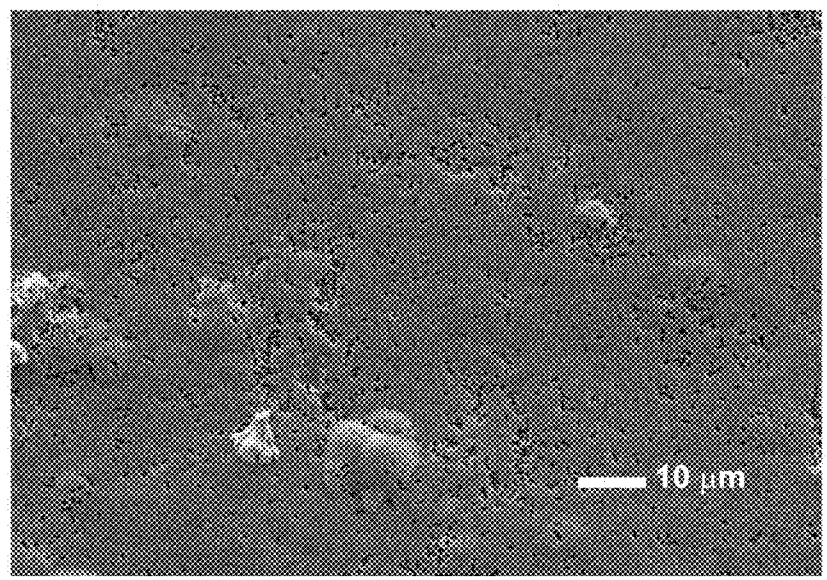
FIGS. 16A and 16B provide SEM images of the remineralized dentin slices after 10 days of treatment with peptide-chitosan hydrogel P26-CS (200 μg/ml).
Figure 16B:
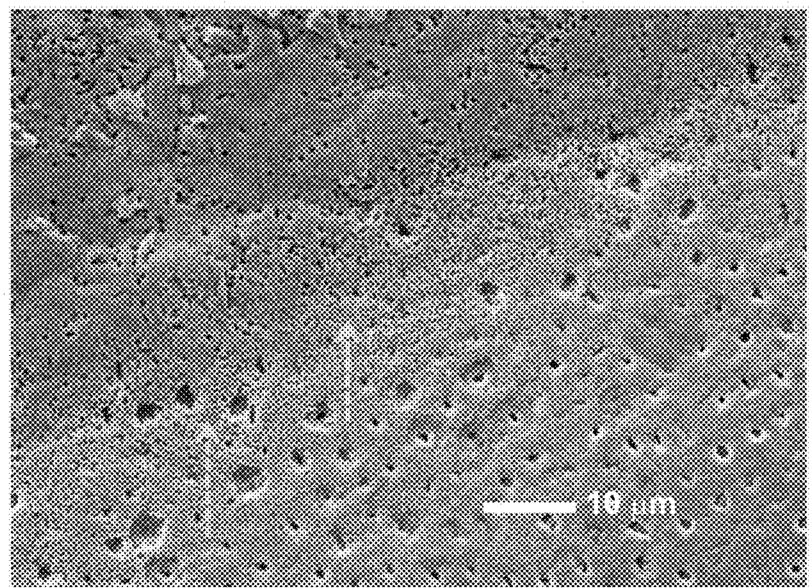

FIG. 11 provides SEM images of the remineralized dentin slices after 5 days of treatment with peptide-chitosan hydrogel LRAP-CS. FIG. 12 provides SEM images of the remineralized dentin slices after 5 days of treatment with peptide-chitosan hydrogel P32-CS. FIG. 13 provides SEM images of the remineralized dentin slices after 5 days of treatment with peptide-chitosan hydrogel P26-CS. FIGS. 14A and 14B provide SEM images of the remineralized dentin slices after 10 days of treatment with peptide-chitosan hydrogel LRAP-CS. FIGS. 15A and 15B provide SEM images of the remineralized dentin slices after 10 days of treatment with peptide-chitosan hydrogel P32-CS. Areas of transition have been shown via dotted arrows as the mineralization advances from the occlusion of the tubules to the regeneration of enamel-like apatitic crystallites on the dentin surface. FIGS. 16A and 16B provides SEM images of the remineralized dentin slices after 10 days of treatment with peptide-chitosan hydrogel P26-CS. Areas of transition have been shown via dotted arrows as the mineralization advances from the occlusion of the tubules to the regeneration of small crystallites on the dentin surface. Narrowing of the peritubular dentin was observed followed by occlusion of the tubules. There was no apatitic layer formed at the end of 5 days of treatment with peptide-gel.

Figure 17A:
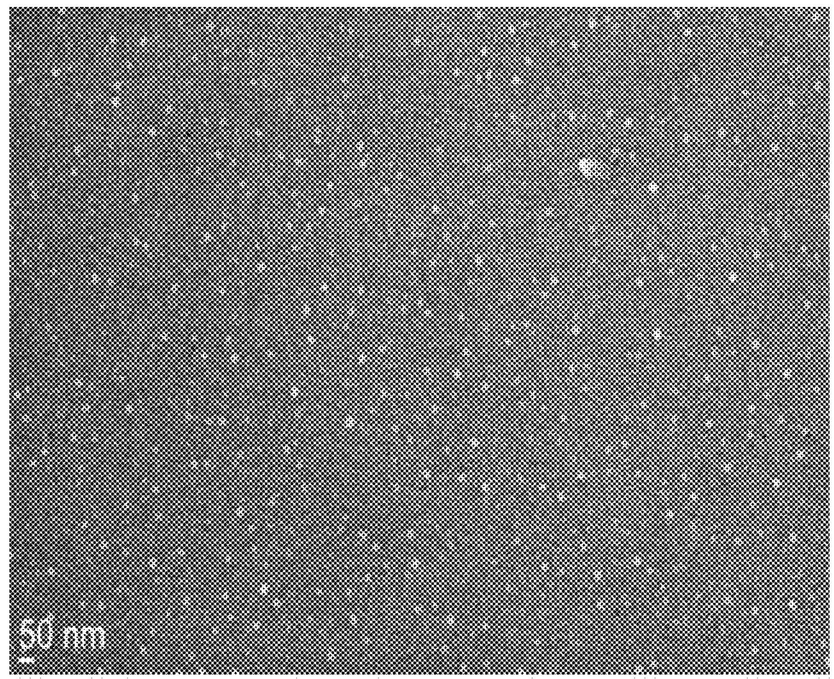
FIG. 17A is a TEM image depicting the uniformly-dispersed spherical assemblies of amelogenin-inspired peptide (P32) formed at pH 7.4, in HEPES buffer, at 25° C.
Figure 17B:
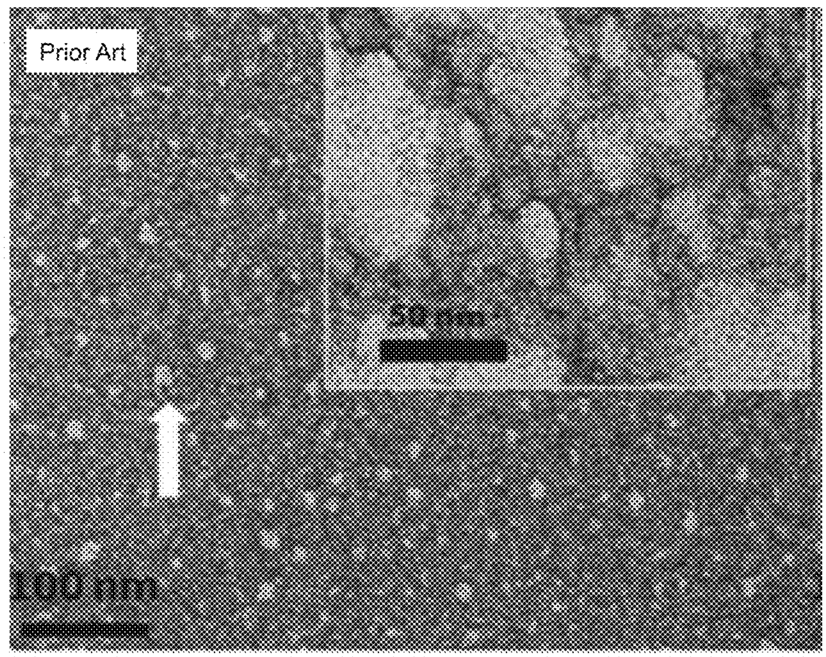
FIG. 17B is a TEM image of a prior art assembly pattern of full-length recombinant porcine amelogenin (rP172).
Figure 18A:
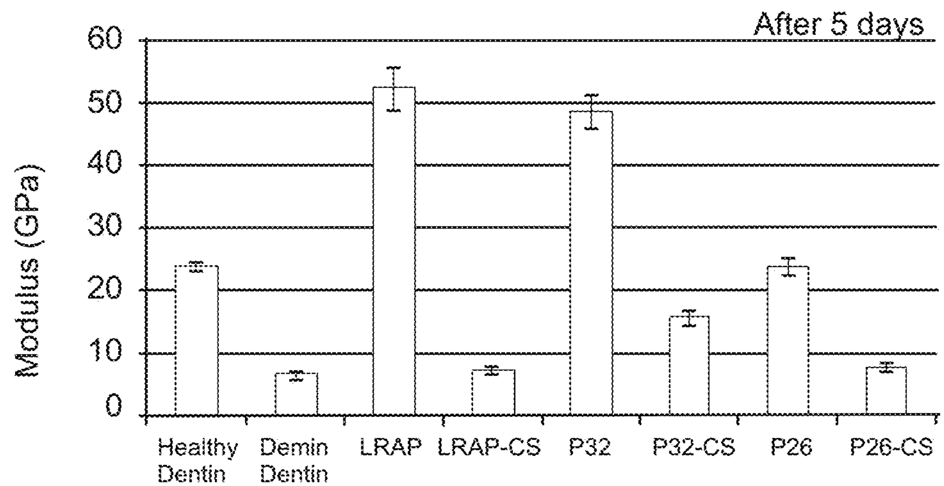
FIGS. 18A, 18B, 18C, and 18D provide nanoindentation test results showing changes in the modulus (A, B) and hardness (C, D) of the newly regenerated layer after being treated with peptide only and peptide-chitosan hydrogel for 5 and 10 days.
Figure 18B:
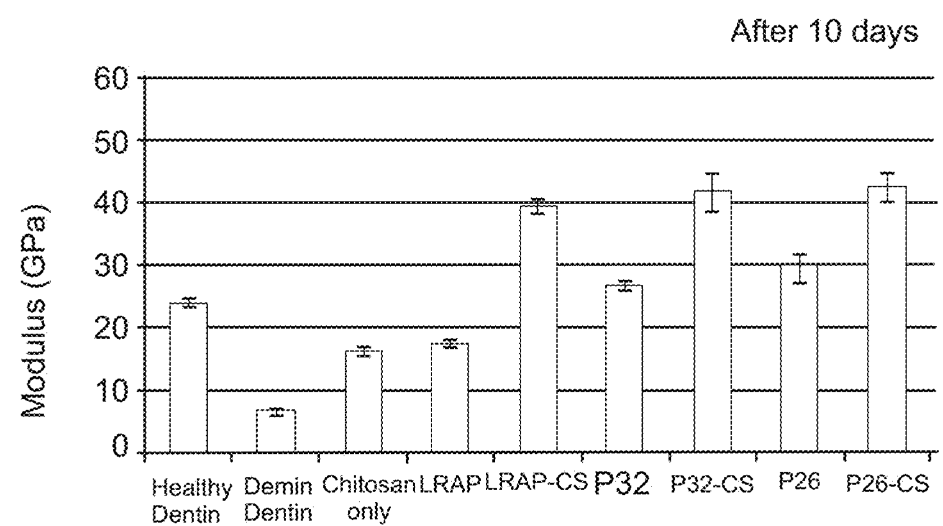
Figure 18C:
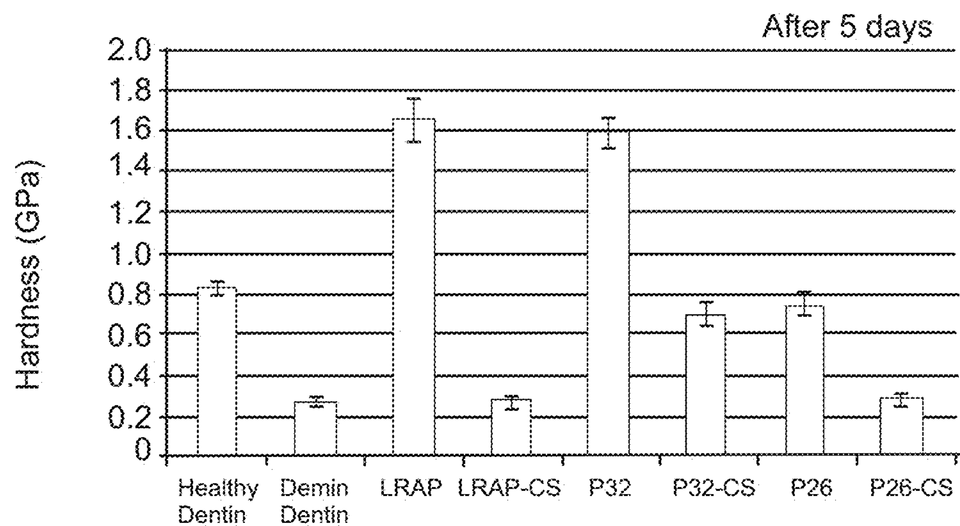
Figure 18D:
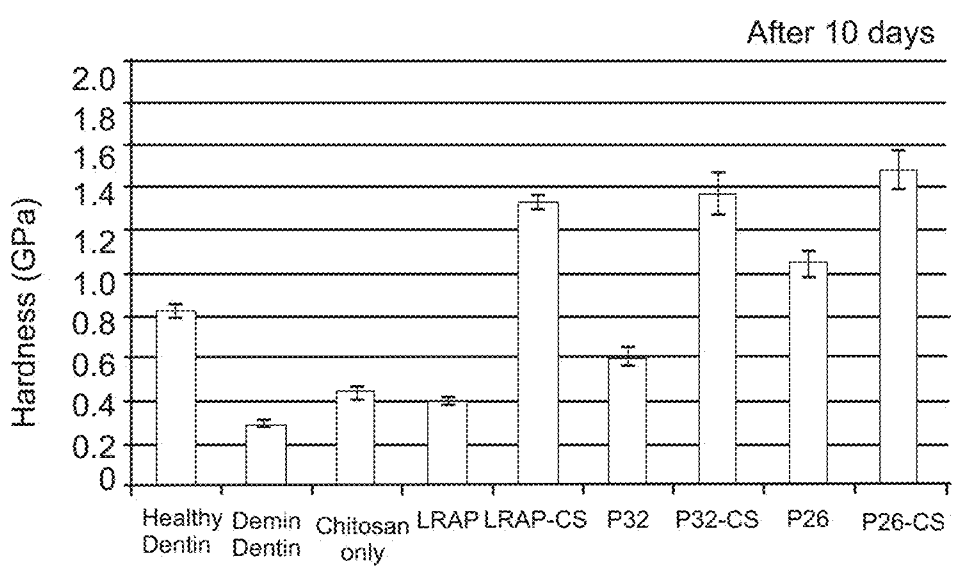

FIG. 17A provides a TEM image depicting the uniformly-dispersed spherical assemblies of amelogenin-inspired peptide (P32) formed at pH 7.4, in HEPES buffer, at 25° C. This characteristic morphology is similar to the assembly pattern of full-length recombinant porcine amelogenin (rP172) as seen in previous studies (FIG. 17B). (Ref: doi:10.1016/j.jsb.2011.07.016).

FIGS. 18A, 18B, 18C, and 18D provide nanoindentation test results showing changes in the modulus (A,B) and hardness (C, D) of the newly regenerated layer after being treated with peptide only and peptide-chitosan hydrogel for 5 and 10 days. Treatment with LRAP and P32 restored surface hardness of dentin lesions in 5 days. A highly mineralized dense layer was formed with superior mechanical properties than healthy dentin. Treatment with peptide-chitosan gel took ~10 days to significantly improve the mechanical properties of dentin lesions.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A polypeptide comprising the amino acid sequence of SEQ ID NO: 10 or SEQ ID NO: 11, with up to 10 conservative amino acid substitutions.

2. The polypeptide of claim 1 having 1 to 5 conservative amino acid substitutions.

3. A composition for treating dental caries, early dental carious and erosive lesions, and enamel defects resulting from genetic diseases, the composition comprising:

a polypeptide comprising the amino acid sequence of SEQ ID NO: 10 or SEQ ID NO: 11;

a chitosan; and water.

4. The composition of claim 3 further comprising a sufficient amount of a pH adjusting component such that the composition has a pH greater than about 6.0, the composition forming an organized mineral layer when contacting a dental lesion.

5. The composition of claim 3 wherein the polypeptide is present in an amount from about 0.03 percent to about 0.4 percent of the total weight of the composition and the chitosan is present in an amount from about 0.2 to about 3 percent of the total weight of the composition.

6. The composition of claim 5 further comprising:

a calcium-containing compound that provides calcium ion when dissolved in water; and a phosphate containing compound that provides phosphate ions when dissolved in water.

7. The composition of claim 6 wherein the calcium-containing compound is present in an amount from about 0.01 percent to about 0.2 percent of the total weight of the composition and the phosphate containing compound is present in an amount from about 0.01 percent to about 0.2 percent of the total weight of the composition.

8. The composition of claim 3 wherein the composition is a hydrogel.

9. The composition of claim 3 further comprising additional protein components.

10. The composition of claim 9 wherein the additional protein components are selected from the group consisting of enamelin, ameloblastin, enamel proteases, chitosanolytic enzymes, and combinations thereof.

11. The composition of claim 10 wherein the additional protein components are individually or collectively present in an amount from about 0.005 percent to about 0.1 percent of the total weight of the composition.

* * * * *

UNITED STATES PATENT AND TRADEMARK OFFICE

CERTIFICATE OF CORRECTION

PATENT NO. : 9,962,465 B2
APPLICATION NO. : 15/202882
DATED : May 8, 2018
INVENTOR(S) : Moradian-Oldak et al.

It is certified that error appears in the above-identified patent and that said Letters Patent is hereby corrected as shown below:

In the Specification

Column 1, Line 15:
After "STATEMENT REGARDING FEDERALLY SPONSORED RESEARCH OR DEVELOPMENT":
Delete:
"The invention was made with Government support under Contract No. (301)594-7703 awarded by the National Institute of Dental and Craniofacial Research. The Government has certain rights to the invention."

And Insert:
--This invention was made with government support under R01 DE013414 awarded by the National Institutes of Health. The government has certain rights in the invention.--

Signed and Sealed this
Twenty-seventh Day of May, 2025

Coke Morgan Stewart
*Acting Director of the United States Patent and Trademark Office*